(12) United States Patent
Breipohl et al.

(10) Patent No.: US 7,084,250 B2
(45) Date of Patent: Aug. 1, 2006

(54) PROCESS FOR THE PREPARATION OF ACETYL-AMIDINIOPHENYLALANYL-CYCLOHEXYLGLYCYL-PYRIDINIOALANINAMIDES

(75) Inventors: Gerhard Breipohl, Frankfurt (DE); Wolfgang Holla, Kelkheim (DE); Heiner Jendralla, Frankfurt (DE); Gerhard Beck, Frankfurt (DE)

(73) Assignee: Sanofi-Aventis Deutschland GmbH, Frankfurt Am Main (DE)

( * ) Notice: Subject to any disclaimer, the term of this patent is extended or adjusted under 35 U.S.C. 154(b) by 204 days.

(21) Appl. No.: 10/869,076

(22) Filed: Jun. 17, 2004

(65) Prior Publication Data

US 2004/0225109 A1    Nov. 11, 2004

Related U.S. Application Data

(63) Continuation of application No. 09/769,487, filed on Jan. 26, 2001, now abandoned.

(30) Foreign Application Priority Data

Jan. 28, 2000    (DE) .............................. 100 03 586

(51) Int. Cl.
*C07K 5/08*    (2006.01)
(52) U.S. Cl. ................. 530/331; 530/333; 530/338; 514/19; 562/553; 546/1
(58) Field of Classification Search ............... 530/331, 530/333, 338; 562/553; 514/19; 546/1
See application file for complete search history.

(56) References Cited

U.S. PATENT DOCUMENTS

| | | | |
|---|---|---|---|
| 4,297,344 A | 10/1981 | Schwinn et al. | |
| 4,440,679 A | 4/1984 | Fernandes et al. | |
| 4,623,717 A | 11/1986 | Fernandes et al. | |
| 5,849,510 A | 12/1998 | Al-Obeidi et al. | |

FOREIGN PATENT DOCUMENTS

| | | |
|---|---|---|
| DE | 29 16 711 | 11/1980 |
| EP | 1 008 350 A1 | 6/2000 |
| WO | WO 95/29189 | 11/1995 |
| WO | WO 97/22712 | 6/1997 |

OTHER PUBLICATIONS

Derwent Abstract of DE 2916711 A.
Beller, M., et al., "Efficient Chemoenzymatic Synthesis of Enantiomerically Pure α-Amino Acids," *Chem. Eur. J.*, 4:5:935-941, 1998.
Chenault, H. K., et al., "Kinetic Resolultion of Unnatural and Rarely Occurring Amino Acids: Enantioselective Hydrolysis of N-Acyl Amino Acids Catalyzed by Acylase I," *J. Am. Chem. Soc.*, 111:16:6354-6364, 1989.
Döbler et al., "Unusual Amino Acids VII. Asymmetric Synthesis of 3- and 4-Pyridylalanines," *Tetrahedron: Asymmetry*, 7:117-125, 1996.
Drauz, K., et al., "Enzyme Catalysis in Organic Synthesis," *VCH*, B.2.3., pp. 393-399, 1995.
Jendralla, H., et al., "Efficient Kg-Scale Synthesis of Thrombin Inhibitor CRC 220," *Tetrahedron*, 51:44:12047-12068, 1995.
Ojima, I., "Catalytic Asymmetric Synthesis," *VCH*, Appendix, pp. 445-447, 1993.
Verkhovskaya, M. A., et al., "Enzymic methods of resolving racemates of amino acids and their derivatives," *Russian Chemical Reviews*, 60:10:1163-1179, 1991.

*Primary Examiner*—David Lukton
(74) *Attorney, Agent, or Firm*—Finnegan, Henderson, Farabow, Garrett & Dunner, L.L.P.

(57) ABSTRACT

The present invention relates to a process for the preparation of acetyl-amidiniophenylalanyl-cyclohexylglycyl-pyridinioalaninamides of the formula I,

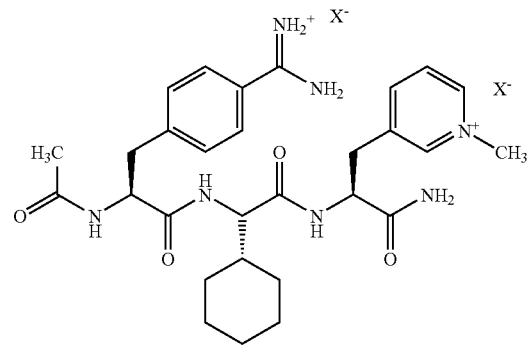

in which the anions X are physiologically acceptable anions, and their analogs, which are effective inhibitors of the blood coagulation factor Xa and which can be used, for example, for preventing thromboses. The process according to the invention comprises the coupling of 2-[2-acetylamino-3-(4-amidinophenyl)propionylamino]-2-cyclohexylacetic acid, which is obtained from 2-[2-acetylamino-3-(4-cyanophenyl)acryloylamino]-2-cyclohexylacetic acid by asymmetric hydrogenation and conversion of the cyano group into the amidine, or a salt thereof, with a 3-(2-amino-2-carbamoyl-ethyl)-1-methylpyridinium salt or a salt thereof. The invention furthermore provides starting materials and intermediates for this process, processes for their preparation and acetyl-(S)-4-amidiniophenylalanyl-(S)-cyclohexylglycyl-(S)-(1-methyl-3-pyridinio)alaninamide as ditosylate salt.

16 Claims, No Drawings

PROCESS FOR THE PREPARATION OF ACETYL-AMIDINIOPHENYLALANYL-CYCLOHEXYLGLYCYL-PYRIDINIOALANINAMIDES

This is a continuation application of U.S. application Ser. No. 09/769,487, filed Jan. 26, 2001 now abandoned, which claims benefit of priority of German Patent Application No. 100 03 586.8, filed on Jan. 28, 2000, both of which prior applications are incorporated herein by reference.

The present invention relates to a process for the preparation of acetyl-amidiniophenylalanyl-cyclohexylglycyl-pyridinioalaninamides of the formula I,

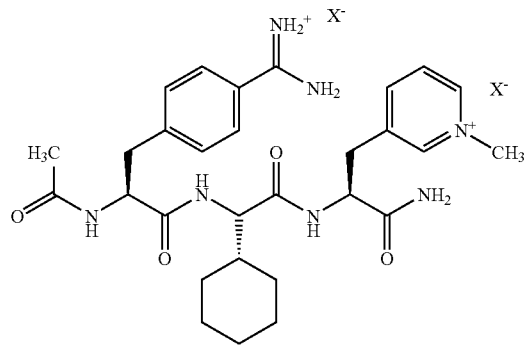

in which the anions X are physiologically acceptable anions, and their analogs, which are effective inhibitors of the blood coagulation factor Xa and which can be used, for example, for preventing thromboses. The process according to the invention comprises the coupling of 2-[2-acetylamino-3-(4-amidinophenyl)propionylamino]-2-cyclohexylacetic acid, which is obtained from 2-[2-acetylamino-3-(4-cyanophenyl) acryloylamino]-2-cyclohexylacetic acid by asymmetric hydrogenation and conversion of the cyano group into the amidine, or a salt thereof, with a 3-(2-amino-2-carbamoylethyl)-1-methylpyridinium salt or a salt thereof. The invention furthermore provides starting materials and intermediates for this process, processes for their preparation and acetyl-(S)$_4$-amid iniophenylalanyl-(S)-cyclohexylglycyl-(S)-(1-methyl-3-pyrid inio)alaninamide as ditosylate salt.

In certain clinical situations, such as, for example, deep vein thrombosis, high risk of myocardial infarction or stable or unstable angina pectoris, disturbances of the blood coagulation system and the formation of thromboses may result in a fatal course. However, in the prevention of thromboses, it is not desirable to inhibit the blood coagulation system excessively or even completely, since this may result in life-threatening bleeding. The coagulation inhibitors that are currently in use, such as heparin, aspirin or hirudine, do not have an optimum property profile, since they can lead to complications by bleeding and, in some of the clinical situations mentioned, are not able to prevent vascular occlusion. Animal experiments have shown that specific inhibitors of the blood coagulation enzyme factor Xa prevent the formation of thrombi reliably without bleeding occurring, as is observed when direct thrombin inhibitors are used. The compounds of the formula I and analogs thereof are specific and highly potent inhibitors of factor Xa which are effective following intravenous, subcutaneous and oral administration.

Compounds of the formula I and analogs thereof are described in WO-A-95/29189 and the corresponding U.S. Pat. No. 5,849,510. According to WO-A-95/29189, they are prepared by solid-phase synthesis using protective-group techniques where 3-pyridylalanine is coupled to a resin using a Knorr linker and then coupled with cyclohexylglycine, the pyridine nitrogen atom is quaternized, the dipeptide is coupled with acetyl-4-amidinophenylalanine, prepared from 4-cyanophenylalanine, and the product is, following cleavage from the resin, purified by chromatography. This solid-phase process is unsuitable for preparing multi-kg quantities required for development tasks, such as toxicological and clinical studies, or even for the synthesis on an industrial scale.

A pharmaceutically active compound is acceptable as development product and for later use in patients only if the preparation can be carried out on the required scale and with adequate purity, where purity, in the case of compounds having centers of asymmetry, includes in particular also stereochemical purity. The compounds of the formula I contain a peptidic dication carrying positive charges in amidinium group and the N-methylpyridinium group. Among the compounds of the formula I with different anions X$^-$ such as acetate, chloride, fumarate, benzoate, tartrate, maleate, trifluoroacetate, tosylate, sulfate or pamoate, only the trifluoroacetate salt (compound of the formula I, X$^-$=CF$_3$CO$_2^-$) was found to be crystalline. However, the thermal stability of the trifluoroacetate salt is insufficient, its shelf-life is unsatisfactory and from a physiological point of view, the salt is less preferred for long-term use. The X-ray powder diagrams of all the other salts of the compound I were found to be notoriously amorphous. The amorphous nature of the salts is a considerable problem in the preparation of a compound of the formula I on a relatively large scale, since it renders recrystallization impossible and fractional precipitation is the only purification method feasable for use on a large scale. However, the purification efficiency of a precipitation is, of course, a lot lower than that of a crystallization, and it is therefore necessary to prepare even the crude compound of the formula I with a suitable anion X in a reaction that proceeds as smoothly as possible, so that in the end a product of clinically acceptable purity can be obtained by fractional precipitation. However, the preparation process naturally also has to be acceptable with respect to factors such as, for example, yield, the number of steps or the availability and the price of the starting materials.

A process for preparing the compounds of the formula I which is not carried out on a solid phase is described in WO-A-97/22712. In this process, the three amino acid units contained in the compounds of the formula I are linked in the same order as in the process of WO-A-95/29189. (S)-3-pyridylalanine, protected at the amino group by a tert-butoxycarbonyl group (Boc), is initially converted into the amide, which is then, after removal of the protective group, coupled with (S)-N-Boc-cyclohexylglycine, the protective group is removed, the dipeptide is coupled with acetyl-(S)-4-cyanophenylalanine and the cyano group in the resulting tripeptide is converted, by reaction with hydrogen sulfide, methyl iodide and ammonia, into the amidine, and the pyridine nitrogen atom is quaternized. The product is isolated in the form of the trifluoroacetic acid salt, by evaporation of the reaction solution obtained in the last reaction step, dissolving the residue, addition of trifluoroacetic acid, filtration and freeze- drying. However, it is found that the purity of the product obtained by this process, including the stereochemical purity, does not meet the requirements, necessitating a complicated chromatographic purification which involves heavy losses and is unacceptable when conducting the process on a large scale. To avoid possible objections from a physiological point of view with respect to the trifluoroacetate anion, it is furthermore necessary to convert the product into a different salt using ion exchange chromatography. Moreover, the process has considerable technical disadvantages, for example the use of solvents such as diethyl ether or hexane or working at low temperatures, and the use of expensive starting materials (small amounts of the three enantiomerically pure unnatural a-amino acids (S)-3-pyridylalanine, (S)-cyclohexylglycine and (S)-4-amidinophenylalanine (or (S)-4-cyanophenylalanine; the amidino group can be formed from the cyano group) contained as building blocks in the compounds of the formula I are commercially available, but these compounds are very expensive). Accordingly, there is still a need for a smooth-running process for the large-scale preparation of compounds of the formula I having a suitable anion X.

This object is achieved by the process for the preparation of compounds of the formula I according to the present invention, which comprises converting the compound of the formula II by catalytic hydrogenation and conversion of the cyano group into the amidino group into the compound of the formula III or its salt with the acid HX, followed by reaction of the compound of the formula III or its salt with a compound of the formula IV or its salt with the acid HX to give the compound of the formula I, where the anions X are physiologically acceptable anions.

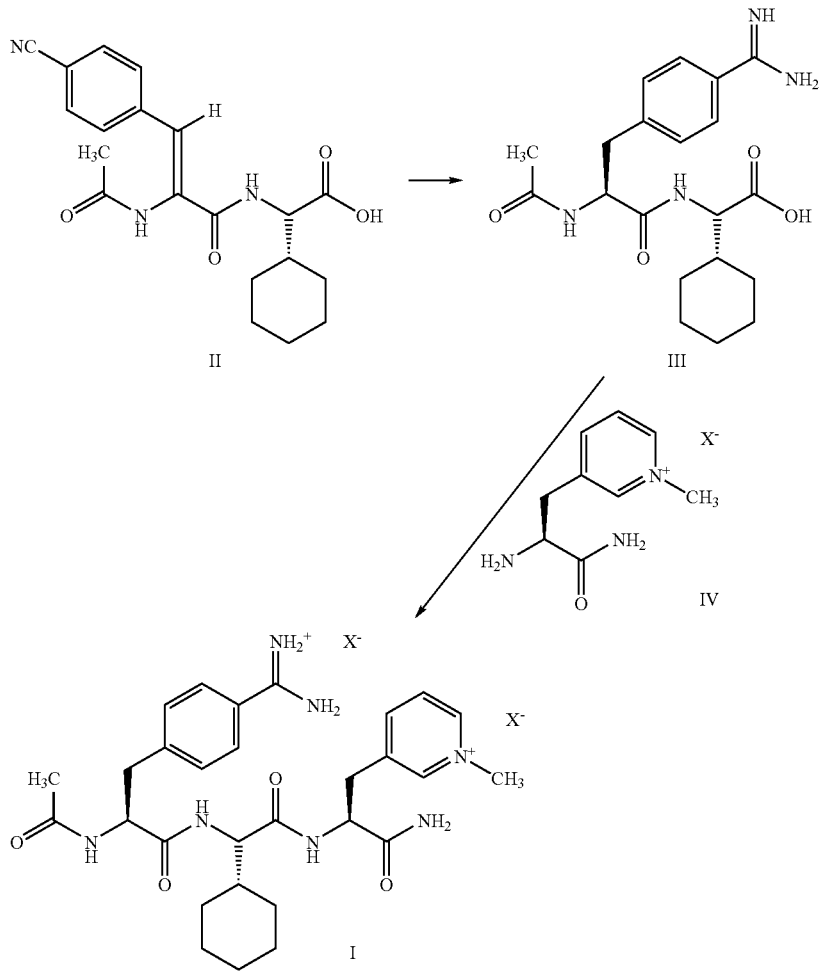

Whereas in the known processes, the molecule of the formula I is constructed by coupling the C-terminal dipeptide of pyridylalanine and cyclohexylglycine with the N-terminal amino acid amidinophenylalanine (or cyanophenylalanine), in the process according to the invention, the molecule is synthesized by coupling the N-terminal dipeptide of amidinophenylalanine and cyclohexylglycine with the C-terminal amino acid pyridylalanine. Moreover, in the process according to the invention, in the dipeptide which is used for this coupling, the structural unit CH—CO—NH—CH—CO, which has two centers of chirality which are sensitive to epimerization, is not formed in a coupling reaction of two chiral α-amino acids as in the known processes, but by asymmetric hydrogenation. In the process according to the invention, the peptide coupling is clean and quantitative, with inexpensive reagents being used. Epimerization is very low. The compounds of the formula I are obtained in high yield and in high chemical purity and stereochemical purity by fractional precipitation. Chromatographic purifications or expensive and complicated technologies, such a freeze-drying, are not necessary to obtain the desired purities.

The present invention also provides processes which are analogous to the above process and in which, using starting materials having a different configuration, stereoisomers of the compounds of the formula I are prepared, for example compounds in which the center of chirality in the amidinophenylalanine unit has the (R) configuration and/or the center of chirality in the cyclohexylglycine unit has the (R) configuration and/or the center of chirality in the pyridylalanine unit has the (R) configuration, or compounds which, on one or more of the centers of chirality, are present as (RS) mixtures. The invention furthermore provides processes which are analogous to the above processes and in which, using the appropriate starting materials, analogs of compounds of the formula I (and their stereoisomers) are prepared, for example compounds which, instead of the methyl group in the acetylamino group in the amidinophenylalanine unit, contain a ($C_1$–$C_4$)-alkyl group and/or, instead of the Methyl group at the quarternary pyridine nitrogen atom, contain a ($C_1$–$C_4$)-alkyl group, examples of such ($C_1$–$C_4$)-alkyl groups being methyl, ethyl, n-propyl, isopropyl, n-butyl, isobutyl and tert-butyl.

Thus, the invention also relates to processes for the preparation of compounds of the formula I':

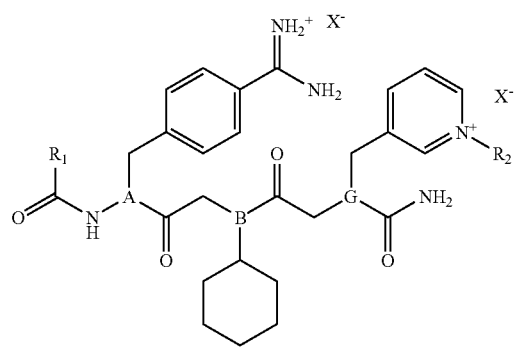

wherein
$R_1$ is $C_1$–$C_4$ alkyl;
$R_2$ is $C_1$–$C_4$ alkyl;
A is CH in the R or S configuration;
B is CH in the R or S configuration; and
G is CH in the R or S configuration.

The processes for the preparation of a compound of the formula I' comprise converting a compound of the formula II' into a compound of the formula III' or its salt with an acid HX, the compound of formula II' having the structure:

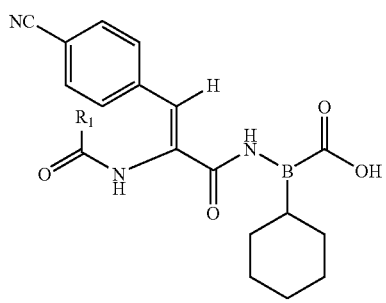

wherein
$R_1$ and B have the same meanings as in the formula I',
said converting comprises catalytic hydrogenation and conversion of the cyano group into an amidino group;
the compound of the formula III' having the structure:

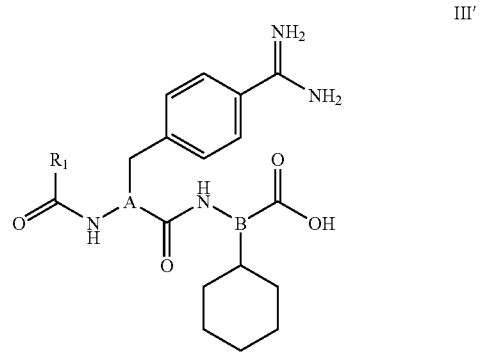

wherein
$R_1$, A, and B have the same meanings as in the formula I';
followed by reacting the compound of the formula III' or its salt with the acid HX with a compound of the formula IV' or its salt with the acid HX:

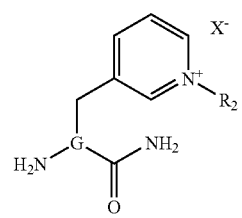

wherein
$R_2$ and G have the same meanings as in the formula I',
to give a compound of the formula I',
wherein the anions $X^-$ of the formulae I' and IV' and of the acid HX are physiologically acceptable anions, and are identical or different.

Physiologically acceptable anions X in the compounds of the formulae I and IV and in the acid HX can be, for example, chloride, bromide, iodide, methanesulfonate, toluene-4-sulfonate, acetate, benzoate and others. In the case of polyvalent anion, for example sulfate, X is an anion equivalent. X is preferably an anion to which there are no objections from a physiological point of view, even if the compounds of the formula I are used in relatively high doses and for a relatively long period of time, and/or which imparts to the compounds of the formula I favorable properties with respect to pharmaceutical processing and the pharmacological action, for example a suitable solubility in water, and/or which imparts to the compounds of the formulae I and IV favorable properties with respect to technically conducting of the process according to the invention, for example simplicity of the process, suitable solubilities in the solvents used, the fact that they are easy to precipitate and/or easy to filter, etc. In a preferred embodiment of the present invention, X is toluene-4-sulfonate (=4-methylbenzenesulfonate=4-$CH_3$—$C_6H_4$—$SO_3^-$=tosylate=TosO$^-$) or iodide particularly preferred embodiment, X is toluene-4-sulfonate.

Thus, in this particularly preferred embodiment, the invention relates to a process for the preparation of the compound of the formula I in the form of the ditosylate salt, i.e. the compound of the formula Ia,

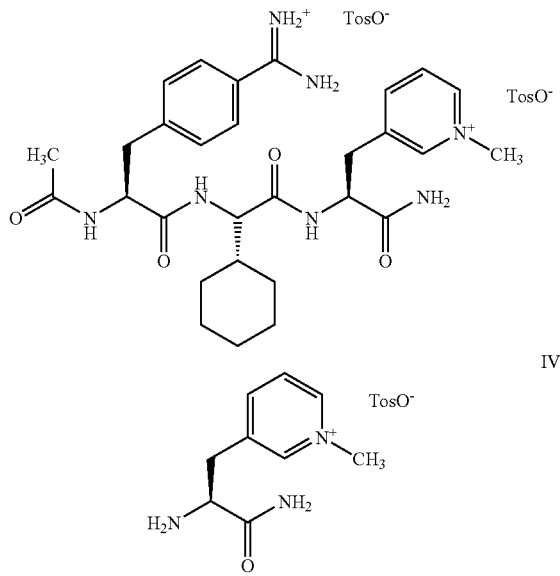

which comprises converting the compound of the formula II by catalytic hydrogenation and conversion of the cyano group into the amidino group into the compound of the formula III or its toluene-4-sulfonic acid salt and reacting the compound of the formula III or its toluene sulfonic acid salt with the compound of formula IVa or the toluene-4-sulfonic acid salt thereof to give the compound of the formula Ia. From a physiological point of view, there are no objections to the tosylate anion contained in the compound of the formula Ia, and the compound of the formula Ia is distinguished, in particular, by particularly good properties when conducting the process according to the invention. The compound of the formula Ia is easy to precipitate and easy to filter and is obtained in a particularly high yield and purity. The present invention also provides the compound of the formula Ia per se and its solvates, for example adducts with water or alcohols, the use of the compound of the formula Ia as an inhibitor of factor Xa or for the treatment, including therapy and prevention, of thromboembolic disorders, such as thromboses, myocardial infarction or angina pectoris, and the use of the compound of the formula Ia for preparing medicaments for these medical applications, and pharmaceutical preparations (or pharmaceutical compositions) comprising an effective amount of the compound of the formula Ia and a pharmaceutically acceptable carrier, i.e. one or more pharmaceutically acceptable excipients and/or additives. More details on the use of the compounds of the formula I including the compound of the formula Ia and on the pharmaceutical preparations comprising them are given in WO-A-95/29189 and U.S. Pat. No. 5,849,510 which are explicitly incorporated into the present disclosure by way of reference.

In addition to the processes described above for the preparation of the compounds of the formula I and for the preparation of the compound of the formula Ia from the compounds of the formulae II and IV or their salts, the present invention relates to a process for preparing the compound of the formula Ia, which comprises reacting the compound of the formula III or its toluene-4-sulfonic acid salt with the compound of the formula IVa or its toluene-4-sulfonic acid salt to give the compound of the formula Ia. For this process, which affords the compound of the formula I in the specific ditosylate form surprisingly in particularly good yield and purity and which is characterized by the fact that it proceeds particularly smoothly and can be carried out in a simple manner, all of the illustrations given above and below for the reaction of the compounds of the formulae III and IV or their salts, i.e. for the peptide coupling step in the context of the process described above, apply correspondingly.

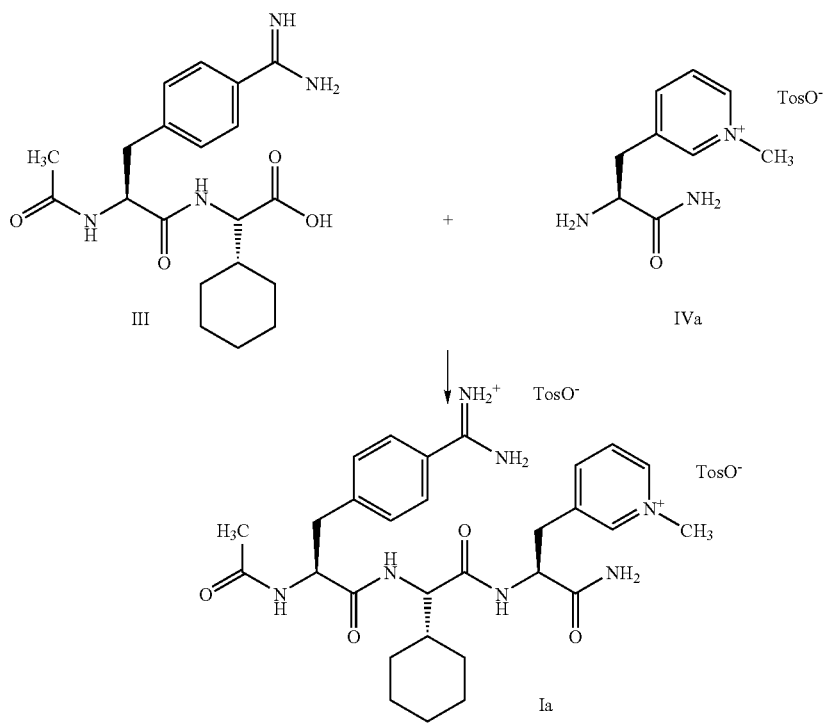

The compounds of the formula I can also be represented by the formula V, which expresses that they can be considered formally as acid addition salts of the acid HX and the monocationic amidino-substituted pyridinium salt contained in the formula V (having a free amidino group (=carbamimidoyl group=amino-imino-methyl group —C(=NH)—NH₂ instead of the protonated, positively charged amidinio group —C(=NH₂⁺)—NH₂ in the formula I).

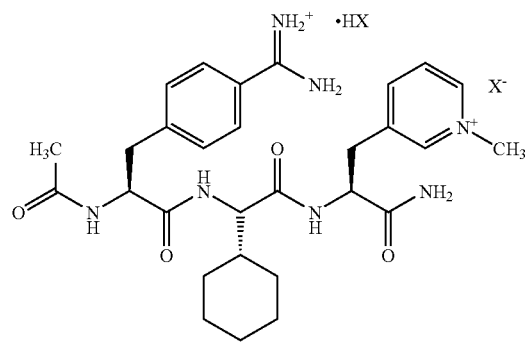

V

Correspondingly, the compounds can also be named in different ways, for example as dicationic pyridinium salts which contain a positively charged amidinio group as a substituent and two negatively charged anions X as counterions, or as acid addition salts of the acid HX and a monocationic pyridinium salt which contains a free amidino group as a substituent and a negatively charged anion X as counterion. Depending on the respective circumstances, other ways of naming may also be appropriate, for example a name derived from peptide nomenclature in which the positively charged amidinium group (=amidinio group) or the free amidine group and the positively charged pyridinium group (=pyridinio group) are considered to be substituents. The compound of the formula Ia, for example, could be referred to as 3-{(S)-2-[(S)-2-((S)-2-acetylamino-3-(4-amidiniophenyl)propionylamino)-2-cyclohexylacetylamino]-2-carbamoylethyl}-1-methylpyridinium ditosylate or as 3-{(S)-2-[(S)-2-((S)-2-acetylamino-3-(4-amidinophenyl)propionylamino)-2-cyclohexylacetylamino]-2-carbamoylethyl}-1-methylpyridinium tosylate toluene-4-sulfonic acid salt, or else as N-acetyl4-aminoimino-methyl)-L-phenylalanyl-L-2-cyclohexylglycyl-3-(1-methylpyridinium-3-yl)-L-alaninamide tosylate toluene-4-sulfonic acid salt.

When carrying out the process according to the invention, the compound of the formula II can be converted into the compound of the formula III by initially hydrogenating the compound of the formula II in a stereoselective manner to give the compound of the formula VI, followed by conversion of the cyano group into amidine, or by initially converting the cyano group into the amidine, followed by stereoselective hydrogenation.

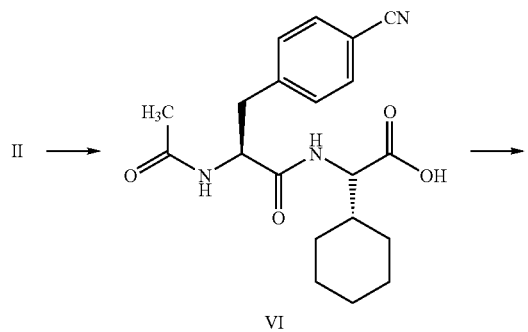

VI

-continued

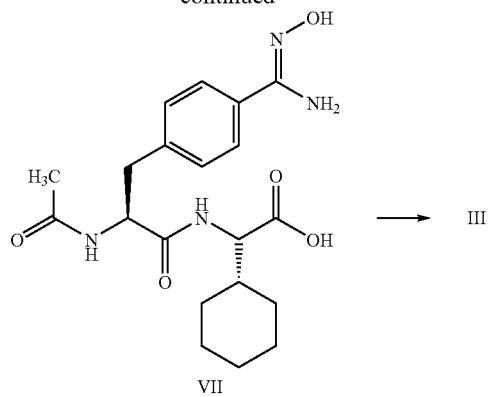

VII

Preferably, the hydrogenation to give the compound of the formula VI is carried out first, followed by conversion of the cyano group into the amidine.

The stereocontrolled hydrogenation of the C=C double bond in the dehydrodipeptide of the formula II can be carried out using selective heterogeneous catalysts or chiral transition metal complexes. It is preferably carried out using chiral metal complexes of rhodium (I) or ruthenium (II), particularly preferably of rhodium (I). The transition metal catalyst can be cationic or neutral, and it can be employed in isolated form or be formed in situ in the hydrogenation medium from the chiral ligand and a precatalyst, for example a rhodium salt such as [Rh(COD)Cl]₂ or [Rh(COD)₂]⁺Y⁻(COD is 1,5-cyclooctadiene, Y here is, for example, tetrafluoroborate). The hydrogenation catalyst can be present in the hydrogenation medium in homogeneously dissolved form, or it can be heterogenized by attachment to a solid support, as a result of which it can be removed easily by filtration after the hydrogenation has ended and be re-used for the next hydrogenation batch. As chiral ligands for the transition metal complex numerous different compounds are suitable. A review of such chiral ligands can be found, for example, in I. Ojima, Catalytic Asymmetric Synthesis, pages 445–447, VCH, New York 1993. In a preferred embodiment of the present invention, a rhodium (I) complex with a chiral phosphine as ligand is used for the asymmetric hydrogenation of the compound of the formula II to give the compound of the formula VI. Particular preference is given to a Rh(I)-(+)-BPPM catalyst, i.e. a rhodium (I) catalyst which comprises, as chiral ligand, (+)-(2R,4R)-1-tert-butyloxycarbonyl-4-diphenylphosphino-2-(diphenylphosphinomethyl)-pyrrolidine (in a molar ratio rhodium:ligand=1:1). The catalyst is preferably prepared in situ from a rhodium salt and the ligand.

Suitable solvents for the stereoselective hydrogenation of the compound of the formula II to give the compound of the formula VI are, for example, ethers, in particular water-miscible ethers, or lower alcohols, such as methanol, ethanol or isopropanol. The hydrogenation is particularly preferably carried out in methanol. The hydrogenation is preferably carried out at temperatures of from about 20 to about 60° C., particularly preferably from about 30 to about 50° C., for example at about 40° C. The hydrogen pressure that is established depends on the apparatus used; it is preferred to establish a hydrogen pressure of from about 1 to about 20 bar, particularly preferably from about 5 to about 15 bar, for example about 10 bar. To increase the efficiency of the hydrogenation, the reaction is carried out with substantial exclusion of oxygen and very intensive mixing. The hydrogenation product can be isolated in a simple manner by adding water and filtering off or centrifuging off the resulting precipitate. The asymmetric hydrogenation proceeds with very high stereoselectivity and yield and gives the compound of the formula VI with a diastereomeric excess of 98.4% d.e. of (S,S)-isomer in the crude product and 99.5% d.e. in the isolated product, at an isolated yield of 97%. Moreover, these excellent results are obtained at very high substrate/catalyst ratios of about 2000:1 to about 5000:1.

The present invention also provides the compound of the formula VI per se, i.e. (S)-2-[(S)-2-acetylamino-3-(4-cyanophenyl)propionylamino]-2-cyclohexylacetic acid and its salts, for example alkali metal or alkaline earth metal salts, such as the sodium salt or the potassium salt, the above process for its preparation and its use as intermediate, in particular as intermediate for pharmaceutically active substances.

The cyano group in the compound of the formula VI can be converted into the amidine by various methods known per se to the person skilled in the art, for example by the method described in WO-A-97/22712 which does, however, have a number of disadvantages when carried out on an industrial scale, for example the use of hydrogen sulfide. The conversion is preferably carried out by initially adding hydroxylamine to the cyano group in the compound of the formula VI, with formation of the N-hydroxyamidine intermediate of the formula VII. The compound of the formula VII is then converted in a simple manner by hydrogenolysis, i.e. by reaction with hydrogen in the presence of a hydrogenation catalyst, into the amidine of the formula II. The principle of this reaction sequence is described, for example, in H. Jendralla et al., Tetrahedron 51 (1995) 12047.

The required hydroxylamine is advantageously prepared in situ from a hydroxylammonium salt, for example hydroxylammonium chloride or hydroxylammonium sulfate, and a base, for example a basic sodium or potassium compound or a tertiary amine. The base used for the reaction of the compound of the formula VI with a hydroxylammonium salt is preferably sodium hydrogen carbonate. The hydroxylamine or the hydroxylammonium salt is preferably employed in excess, for example in an amount of from about 1 to about 2 mol per mole of the compound of the formula VI. Suitable solvents for the reaction with hydroxylamine or a hydroxylammonium salt are, for example, lower alcohols. A particularly preferred solvent is methanol. The compound of the formula VII is preferably prepared at temperatures of from about 20 to about 65° C., particularly preferably at temperatures from about 40 to about 60° C. If a hydroxylammonium salt is employed, the added base also converts the carboxylic acid function in the compound of the formula VI or that in the compound of the formula VII into the corresponding salt. If an intermediate isolation of the N-hydroxyamidine of the formula VII is desired, this compound can be isolated in an advantageous manner in the form of a salt at the carboxylic acid function, i.e., if the base used is a sodium compound, in the form of the sodium salt of the carboxylic acid, which can be precipitated by concentrating the reaction mixture and/or admixing with a relatively nonpolar solvent and removed by filtration or centrifugation.

The hydrogenolysis of the compound of the formula VII or a salt thereof to give the compound of the formula III can be carried out under conditions which are customary for catalytic hydrogenations, for example in the presence of a customary noble metal catalyst, such as palladium on carbon. The reaction conditions depend on the apparatus used. The hydrogen pressure can, for example, be in a range of from about 1 to about 30 bar, in particular from about 5 to about 25 bar, and the reaction temperature can be from about 20 to about 70° C., in particular from about 40 to about 60° C. The hydrogenolysis is preferably carried out in an acidic medium. Preferred solvents for the hydrogenolysis are, in particular if the N-hydroxyamidine is employed in the form of a salt, polar solvents, for example lower alcohols or acetic acid. A particularly preferred solvent is acetic acid. The resulting amidine compound of the formula III can be isolated as such (i.e., in free form) or in the form of an acid addition salt (the amidine compound of the formula III as such might not be present in the form having a free amidino group and a carboxylic acid group, which is represented by the formula III, but in the tautomeric form of the formula IIIa, i.e. as betaine or zwitterion, in which the carboxylic acid group is dissociated to the carboxylate anion and the amidine unit is protonated to the amidinium cation).

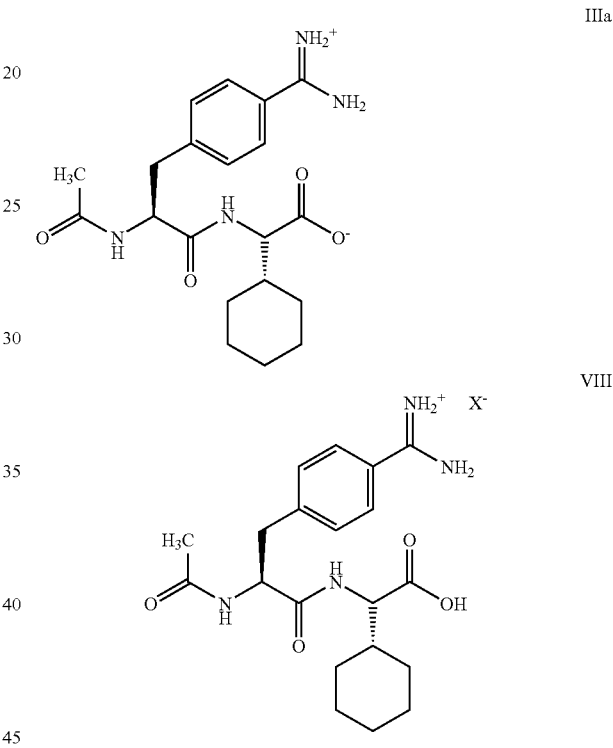

In the presence of an acid, which may be present even during the hydrogenolysis, for example if the solvent used is acetic acid, or which can be added during work-up, the compound of the formula III is obtained as acid addition salt. Thus, using an acid of the formula HX, a salt of the formula VIII is formed, in which the anion X is preferably a physiologically acceptable anion, for example iodide or tosylate. The compounds of the formula VIII are the above-mentioned salts of the acid HX and the compound of the formula III. If the compound of the formula III is to be isolated in the form of an acid addition salt, the acid HX is preferably chosen such that the compound of the formula VIII contains the same anion as the compound of the formula I to be prepared. Thus, if the ditosylate salt of the formula Ia is to be prepared and the compound of the formula III is to be isolated as a salt, preference is given to preparing the amidinium tosylate of the formula VIII where X=TosO⁻, for example by adding toluene-4-sulfonic acid during work-up. As already mentioned, for the peptide coupling with the compound of the formula IV it is possible to use either the compound of the formula III as such, i.e. the betaine (or zwitterion) of the formula IIa, or the amidinium salt of the formula VIII(=salt of HX and the compound of the formula II), both giving similar purities and yields. The compound of the formula III is preferably isolated as betaine (or zwitterion) of the formula IIIa and used as such for the peptide coupling. If the hydrogenolysis is carried out in acetic acid, the acetic acid salt of the compound of the formula III (=compound of the formula VIII where X⁻=acetate) initially formed can be converted into the betaine by recrystallization from water.

The present invention also provides the compounds of the formula II and their salts and the compounds of the formulae IIIa and VIII per se, i.e. (S)-2-[(S)-2-acetylamino-3-(4-amidinophenyl)propionylamino]-2-cyclohexylacetic acid as betaine (zwitterion) and in the form of their salts, the above process for their preparation and their use as intermediates, in particular as intermediates for pharmaceutically active compounds.

The peptide coupling of the amidine of the formula III (in the form of a salt or preferably in the form of the betaine of the formula IIIa) with the pyridinioalaninamide of the formula IV or a salt thereof to give the compound of the formula I can be carried out by customary coupling methods known to the person skilled in the art. The pyridinioalaninamide is preferably employed in the form of a salt with the acid HX, i.e. in the form of the dication salts of the formula IX, in which the anions X are preferably physiologically acceptable anions.

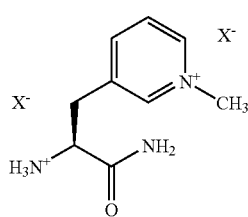

IX

The anion X in the compound of the formula IV or the compound of the formula IX and, if the compound of the formula III is employed in the form of a salt of the formula VIII, also the anion in the compound of the formula VIII is preferably the anion of the compound of the formula I to be prepared, i.e., in the case of the preparation of the compound of the formula Ia, the tosylate anion. If neither the compound of the formula III nor the compound of the formula IV are employed for the peptide coupling in the form of a salt with the acid HX, the second equivalent of the anion X, which is required for preparing the compound of the formula I in addition to the equivalent of the anion X introduced by the compound of the formula IV, can be added in the form of an equivalent of the acid HX or a salt of the acid HX during work-up of the reaction mixture of the peptide coupling.

Examples of peptide coupling agents suitable for activating the carboxylic acid function or carboxylate function in the compound of the formula III (or IIIa or VIII) which may be mentioned are carbodiimides, such as, for example, dicyclohexylcarbodiimide (DCC) or diisopropylcarbodiimide (DIC), or uronium salts, such as O-[(cyano-ethoxycarbonyl-methylene)amino]-N,N,N',N'-tetramethyluronium tetrafluoroborate (TOTU) or O-(7-azabenzotriazol-1-yl)-N,N,N',N'-tetramethyluronium hexafluorophosphate (HATU). Carbodiimides are preferably employed in the presence of hydroxybenzotriazine or hydroxybenzotriazole reagents, such as 3-hydroxy-4-oxo-3,4-dihydro-1,2,3-benzotriazine (=3-hydroxy-1,2,3-benzotriazin-4(3H)-one=HOObt) or 1-hydroxy-1H-benzotriazole (HObt). Preference is given to activating agents and reaction conditions in which epimerizations at the chiral carbon atoms, in particular at the α-position to the carbonyl group in the compound of the formula II, are minimal, so that only few, if any, diastereomeric impurities are formed. Activating agents which are particularly preferred in this respect are HATU, DCC/HOObt and DCC/HObt. In particular with HATU or DCC/HOObt, the coupling gives a product which contains only 0.7–1.5% of the diastereomer in the crude product. Specially preferred, owing to its considerably lower price, is DCC/HOObt. For safety reasons, HOObt is preferably employed on a support, for example on Dicalite®.

The coupling reaction is preferably carried out in a polar solvent (or a solvent mixture). Suitable solvents are protic solvents, such as lower alcohols, for example methanol, ethanol or isopropanol, and from among these alcohols, preference is given to isopropanol, since the risk of a conversion of the C-terminal amide group into the ester is lower than with methanol or ethanol. Particularly preferably, the coupling is carried out in aprotic polar solvents in which the coupling proceeds particularly rapidly and cleanly, for example in amides, such as N,N-dimethylformamide (DMF) or N-methyl-2-pyrrolidone (NMP), or in dimethyl sulfoxide (DMSO). However, it is also possible to use solvents such as, for example, ethyl acetate, tetrahydrofuran (THF) or methylene chloride, in particular also in a mixture with other solvents. Very particularly preferably, the coupling is carried out in DMF or NMP, both of which give excellent coupling results and isolated yields of the compound of the formula I of 85–95% (after two product precipitations). Especially preferably, the coupling is carried out in DMF, since this can be removed more easily from the product. The coupling is preferably carried out at temperatures of from about 0 to about 30° C., particularly preferably at from about 0 to about 25° C., for example by initially stirring the reaction mixture at about 10° C. and then allowing it to warm to room temperature. If, in the preferred embodiment of the coupling step, the compound of the formula III in the form of the zwitterion of the formula IIIa is reacted with the dication salt of the formula IX, a favorable pH (from about 3.3 to 4.2 if X in the compound of the formula IX is tosylate) is generally present during the entire course of the coupling, without the addition of an additional base being required. Optionally, the pH can be adjusted appropriately by adding a base, such as a tertiary amine. If both the compound of the formula III and the compound of the formula IV are employed for the coupling in the form of salts with an acid HX, the peptide coupling requires the addition of at least one equivalent of a base, for example a tertiary amine, such as triethylamine or, preferably, N-ethyldiisopropylamine.

In the preferred embodiment of the coupling step, where the activating agent used is a carbodiimide together with an N-hydroxybenzotriazine or N-hydroxybenzotriazole reagent, such as, for example, HOObt, this reagent can be present in substoichiometric amounts or only catalytic amounts, since the N-hydroxy reagent is regenerated during the reaction of the compound of the formula IV with the activated ester intermediately formed from the compound of the formula III and the N-hydroxy reagent. If, for example, the coupling is carried out using DCC/HOObt, the HOObt is preferably employed in an amount of from about 0.15 to about 1 mol per mole of the compound of the formula III, particularly preferably in an amount of from about 0.2 to about 0.3 mol, for example about 0.25 mol, per mole of the compound of the formula II. The carbodiimide is preferably employed in a slight excess. If the coupling is carried out using DCC/HOObt, for example, preferably an amount of from about 1.1 to about 1.4 mol per mole of the compound of the formula II, particularly preferably an amount from about 1.2 to about 1.3 mol, for example about 1.25 mol, per mole of the compound of the formula III is employed. The order in which the reactants are added is variable. Preference is given to initially charging the compounds of the formula III and IV or their salts, any base that may be added and the N-hydroxy reagent, and to meter in the carbodiimide, for example in the form of a solution in a solvent such as DMF or NMP, over a period of several hours, for example from about 5 to about 10 hours. In this procedure, the coupling, at a reaction temperature of about 10° C. followed by stirring at room temperature, is generally completed rapidly, takes place virtually quantitatively and gives the product in high purity.

For work-up, the reaction mixture is advantageously initially filtered, and the product is then precipitated by adding a suitable organic solvent. If the coupling is carried out in DMF or NMP, the precipitation is preferably carried out using an excess of a lower ketone, such as acetone or methyl ethyl ketone, particularly preferably the DMF solution or NMP solution being added dropwise or by means of a pump to an excess of acetone or methyl ethyl ketone. The precipitated product is isolated by filtration or centrifugation, washed and, if desired for increasing the purity, precipitated a second time or else a third time in an analogous manner (for example by dissolving the product in DMF and precipitating it by pumping the solution into acetone or methyl ethyl ketone). With this procedure, most of the by-products remain in solution, and after two precipitations, for example, the compound of the formula Ia (ditosylate) is obtained in a yield of about 91% and a purity of about 97% (+about 2.4% of the diastereomer).

The starting materials of the formulae II and IV or their salts, which are used in the process according to the invention described above, can be prepared, for example, by the processes described below. In a preferred form of the process according to the invention described above, the starting material of the formula II and/or the starting material of the formula IV or their salts used are prepared by the processes described below or are in part prepared by the processes described below.

anhydride in a solvent, preferably by heating in acetone under reflux. The reaction of the compounds of the formulae XI and XII to give the dehydrodipeptide of the formula II is preferably carried out in alkaline solution, for example with addition of one equivalent (based on the cyclohexylglycine) of a base such as sodium hydroxide or potassium hydroxide, in a mixture of water and a water-miscible organic solvent, for example a ketone, such as acetone, or an ether, particularly preferably in a mixture of acetone and water, at temperatures of from about 30 to about 50° C., for example, at about 40° C. To isolate the product, the reaction mixture is acidified, for example with hydrochloric acid, to a pH of about 2.3 and diluted with water, and the precipitate is filtered off or centrifuged off. With this procedure, the resulting compound of the formula II is present mainly as Z isomer, the percentage of E isomer is <2%. The present invention also provides the compounds of the formulae II and XI and salts of the compound of the formula II per se, in particular the Z forms, the above processes for their preparation and their use as intermediates, in particular as intermediates for pharmaceutically active compounds. Salts of the compound of the formula II which may be mentioned are, for example, alkali metal and alkaline earth metal salts, such as the sodium salt or the potassium salt.

The optically pure (S)-cyclohexylglycine (formula XII) required is advantageously prepared by one of the following three routes. In one route, the starting material used is racemic phenylglycine (formula XIII) which is converted, by hydrogenation of the aromatic ring under standard conditions, into racemic cyclohexylglycine (formula XIV), for example by hydrogenation in the presence of a noble metal catalyst, such as rhodium on carbon, in hydrochloric acid at from about 80 to about 120° C., for example at about 100° C., and at a hydrogen pressure of from about 10 to about 30 bar. The racemic cyclohexylglycine is then acetylated under standard conditions at the amino group using, for example, acetic anhydride in the presence of a base, such as sodium hydroxide, in water at a temperature of from about 0 to about 30° C. and at a pH of at least 11. The racemic N-acetylcyclohexylglycine (formula XV) is then subjected to an enzymatic racemate resolution using an acylase (L-specific aminoacylase, E.C.3.5.1.14), to give optically pure (S)-cyclohexylglycine (formula XII) and N-acetylcyclohexylglycine containing a high excess of the (R) antipode (formula

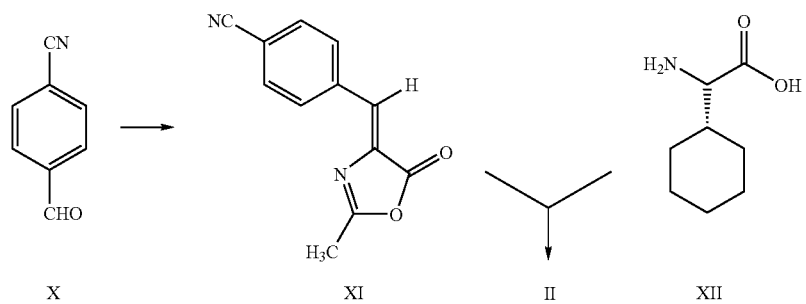

The compound of the formula II can be obtained by reacting the azlactone of the formula XI with (S)-cyclohexylglycine (formula XII). The azlactone of the formula XI, which is essentially present as Z isomer, is formed under standard conditions for the Erlenmeyer azlactone synthesis from 4-formylbenzonitrile (formula X) and N-acetylglycine, for example by heating with sodium acetate and acetic XVI) (see, for example, K. Drauz et al., Enzyme Catalysis in Organic Synthesis, VCH, Weinheim, 1995; M. A. Verkhovskaya et al., Russ. Chem. Rev. 60 (1991) 1163; H. K. Chenault et al., J. Am. Chem. Soc. 111 (1989) 6354). The selective enzymatic deacetylation of the (S)-N-acetyl-cyclohexylglycine in the (RS) mixture can be carried out, for example, using the acylase "Amano" 30 000 in the presence of cobalt(II) chloride in water at a pH of about 7.8 and a temperature of about 38 to 40° C. The cyclohexylglycine that precipitates out is virtually enantiomerically pure (S) isomer. The (R)-N-acetylcyclohexylglycine, which remains in the filtrate, can, after racemization, for example by heating with acetic acid and acetic anhydride at about 115° C., again be subjected to enzymatic deacetylation, so that in the end virtually all of the racemic N-acetylcyclohexylglycine is converted into optically pure (S)-cyclohexylglycine.

N-acetylglycine and acetic anhydride in acetone. The azlactone of the formula XIX can be solvolyzed with water to give N-acetyidehydropyridylalanine, i.e. to the carboxylic acid, or with a lower alcohol, for example a ($C_1$–$C_3$)-alkanol, such as methanol or ethanol, to give a carboxylic acid ester, preferably with methanol to give the methyl ester (compare formula XX). As the subsequent asymmetric hydrogenation is particularly advantageously carried out in an alcohol under acidic conditions, where most or all car-

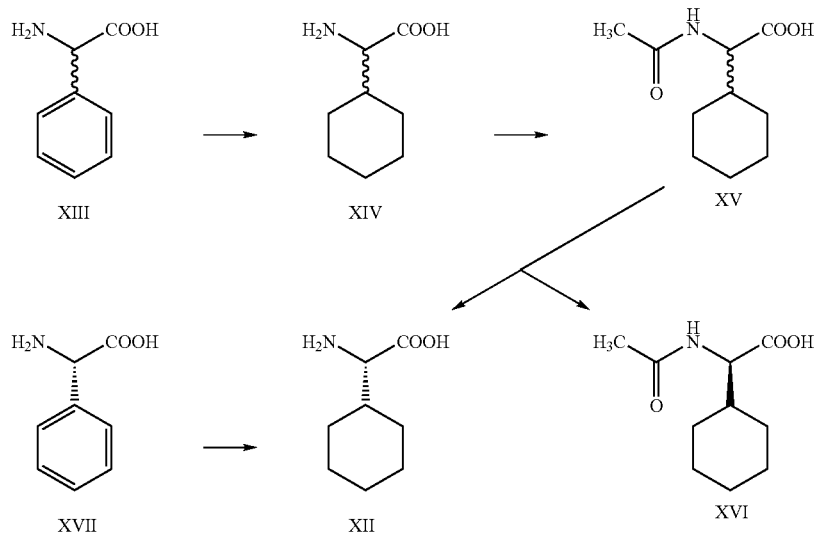

A second possibility of preparing (S)-cyclohexylglycine comprises preparing racemic N-acetylcyclohexylglycine (formula XV) in a one-step process by palladium-catalyzed amidocarbonylation from cyclohexanecarbaldehyde, carbon monoxide and acetamide, followed by the described racemate resolution with an acylase (see M. Beller et al., Chem. Eur. J. 4 (1998) 935).

In the third process for preparing (S)-cyclohexylglycine (formula XII), the phenyl group in enantiomerically pure (S)-phenylglycine (formula XVII) is hydrogenated under racemization-free conditions to the cyclohexyl group. Again, suitable catalysts are noble metal catalysts, such as, for example, rhodium on carbon. The hydrogenation is preferably carried out in acidic medium, for example in a carboxylic acid, such as glacial acetic acid, particularly preferably in a strong acid, such as, for example, 2N hydrochloric acid or sulfuric acid. In such a strong acid, the hydrogenation proceeds rapidly and without any significant racemization at a temperature of from about 60 to about 80° C. and a hydrogen pressure of, for example, about 20 bar. The resulting product is of a similar quality to the product that is obtained from racemic phenylglycine by the process described above. The starting material (S)-phenylglycine is more expensive than the starting material (RS)-phenylglycine, but owing to the lower production costs, the process which uses (S)-phenylglycine as starting material is more advantageous.

The enantiomerically pure starting material of the formula IV or its salt of the formula IX is advantageously prepared starting from pyridine-3-carbaldehyde (formula XVIII), which can be converted under similar conditions as those stated above for the conversion of the compound of the formula X into the compound of the formula XI, into the azlactone of the formula XIX, for example by heating with boxylic acid functions are converted into the ester, and as the solvolysis of the azlactone of the formula XIX with alcohols proceeds more smoothly than that with water, the compound of the formula XIX is preferably solvolyzed using a lower alcohol, particularly preferably methanol. The alcoholysis is preferably carried out in the presence of a weak base, for example a tertiary amine, such as triethylamine, at temperatures of from about 50 to about 65° C. The methyl ester is preferably isolated in the form of an acid addition salt with a strong acid, i.e. in the form of a compound of the formula XX, where the anion Y here is the anion of a strong acid, for example tetrafluoroborate or tosylate. Particularly preferably, the product of the methanolysis of the azlactone of the formula XIX is precipitated as tetrafluoroborate salt by adding tetrafluoroboric acid, for example an aqueous tetrafluoroboric acid solution, up to a pH of about 1.5 to about 2, for example about 1.9, and the product is, after the precipitation has been brought to completion by addition of a nonpolar solvent, for example an ether, such as methyl tert-butyl ether, filtered off or centrifuged off. The compound of the formula XX where Y=$BF_4$ is obtained in high yield (90%) and very high purity (>99.5%).

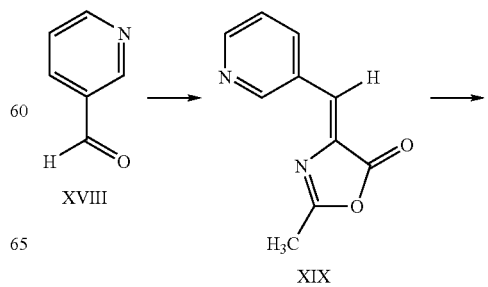

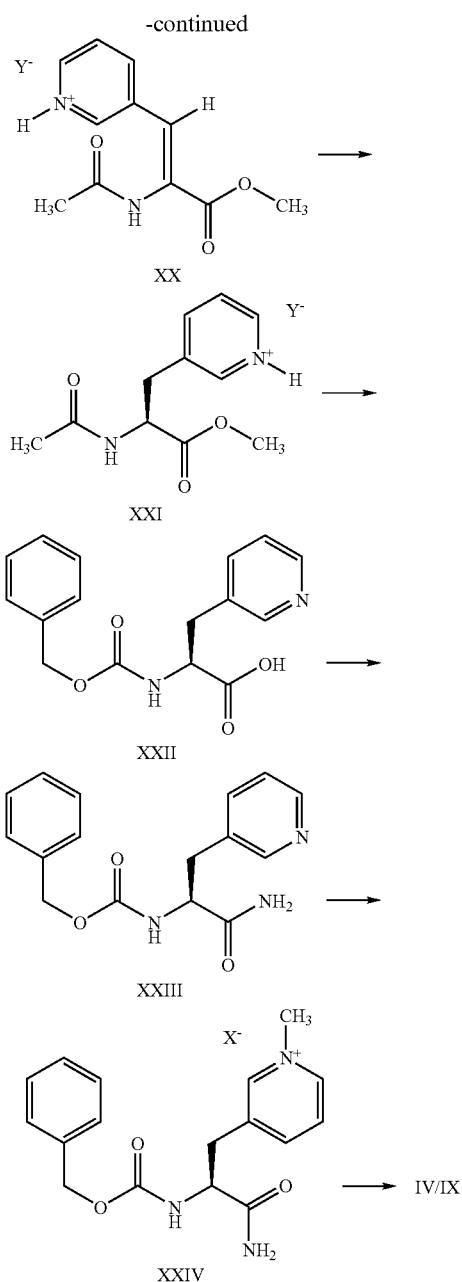

The next step is an asymmetric catalytic hydrogenation of the dehydropyridylalanine derivative of the formula XX to give the optically active amino acid derivative of the formula XXI. As mentioned, in order to obtain a high yield and a short reaction time, this hydrogenation is preferably carried out under acidic conditions, for example in acetic acid, particularly preferably in the presence of a strong acid, for example toluene-4-sulfonic acid or tetrafluoroboric acid, which is employed in at least the stoichiometric amount, for example 1- to 2-times the molar amount, thus converting the pyridine group completely into the pyridinium salt. For the hydrogenation, preference is given to using a pyridinium salt of the formula XX and, if appropriate, additional acid. Particularly preferably, the hydrogenation of the pyridinium salt of the formula XX, in particular the salt where $Y=BF_4$, is carried out in a lower alcohol, specifically methanol, in the presence of about 15 mol % of a strong acid. Preferred acids in whose presence the hydrogenation of the salt of the formula XX is carried out are tetrafluoroboric acid and toluene-4-sulfonic acid, in particular tetrafluoroboric acid, which can be used in the form of an aqueous solution.

With respect to the catalyst for the asymmetric hydrogenation of the compounds of the formula XX to those of the formula XXI, the illustrations given above for the catalysts for the hydrogenation of the compound of the formula II to that of the formula VI apply correspondingly. Thus, the stereocontrolled hydrogenation of the C=C double bond in the compound of the formula XX can likewise be carried out using selective heterogeneous catalysts or using chiral transition metal complexes. It is preferably carried out using chiral metal complexes of rhodium(I) or ruthenium(II), in particular of rhodium(I). The transition metal catalyst can be employed in isolated form or can be formed in situ in the hydrogenation medium, from a chiral ligand and a precatalyst, for example, a rhodium salt, such as $[Rh(COD)Cl]_2$. The catalyst is preferably prepared in situ. As chiral ligands for the transition metal complex again numerous different compounds are suitable. In a preferred embodiment of the present invention, the catalyst used for the asymmetric hydrogenation of the compounds of the formula XX to the compounds of the formula XXI is a rhodium(I) complex having a chiral phosphine as ligand, particularly preferably an Rh(I)-(+)-phenyl-CAPP catalyst, i.e. a rhodium(1) catalyst which contains, as chiral ligand, (+)-(2R,4R)-1-phenylaminocarbonyl-4-diphenylphosphino-2-(diphenylphosphinomethyl)pyrrolidine (in a molar ratio of rhodium:ligand=1: 1). However, suitable for use as ligands in catalyst complexes are also, for example, the abovementioned (+)-BPPM or the aminophosphinephosphinite (+)-PPP (=(+)-propraphos, see C. Döbler et al., Tetrahedron: Asymmetry 7 (1996) 117). Further ligands for suitable catalytically active transition metal complexes are listed, for example, in I. Ojima, Catalytic Asymmetric Synthesis, pages 445–447, VCH, New York 1993.

The hydrogenation of the compound of the formula XX is preferably carried out at temperatures of from about 20 to about 60° C., particularly preferably between about 30 and about 50° C., for example at about 40° C. Again, the hydrogen pressure employed depends on the apparatus used; preference is given to a hydrogen pressure of from about 0.2 to about 20 bar, particularly preferably from 0.2 to about 10 bar, especially preferably of from about 0.5 to about 1 bar, for example about 0.8 bar. In particular when a Rh(I)-phenyl-CAPP catalyst is used, the hydrogenation is, to increase enantioselectivity, preferably carried out at relatively low hydrogen pressure. As explained above for the hydrogenation of the compound of the formula II, here, too, the reaction is carried out with substantial exclusion of oxygen and with very intensive mixing, to increase the efficiency of the hydrogenation. The hydrogenation product of the formula XXI is, in particular in the case of the tetrafluoroborate salt, preferably isolated by crystallization, for example from an alcohol, such as isopropanol. The isolated yield is from about 86 to about 95%, the enantiomeric purity is, depending on the chosen conditions, from about 70% to about 95% e.e. of (S) isomer. For the hydrogenation of the compounds of the formula XX to those of the formula XXI, it is possible to use very high substrate/catalyst ratios of from about 5 000:1 to about 10 000:1, for example about 8 000:1.

In the next step, the methyl ester group in the compounds of the formula XXI is hydrolyzed to give the carboxylic acid group, the acetyl group at the amino group is removed and the amino group is protected in a suitable manner, so that it does not cause any side-reactions during the formation of the carboxamide function. Removal of the acetyl group and hydrolysis of the methyl ester to the free carboxylic acid can be carried out simultaneously by treatment with an acid, for example aqueous hydrochloric acid, such as 1 N hydrochloric acid, or 4N hydrochloric acid, at temperatures of, for example, from about 60 to about 85° C. or of from about 85 to about 90° C. To facilitate the isolation of the product from the aqueous reaction mixture, the free amino group is then advantageously immediately converted into an acylamino group which later can be easily deprotected, for example into the benzyloxycarbonylamino group. Introduction of the benzyloxycarbonyl protective group (=Z group) is preferably carried out using N-benzyloxycarbonyloxysuccinimide (=Z-OSu) in the solvent water/THF in the weakly alkaline range, particularly preferably at a pH of from about 8.0 to about 8.5. After the reaction has ended, the organic solvent is distilled off, a slightly acidic pH, preferably a pH of about 5, is established and the precipitated compound of the formula XXII is filtered off or centrifuged off. If desired, the purity of the compound of the formula XXII can be increased by recrystallization, for example from water, prior to the preparation of the amide of the formula XXIII.

If the enantiomeric purity of the compounds of the formula XXI or the compound of the formula XXII obtainable therefrom by the process described above is insufficient, it is advantageous to cleave the acetyl group from the amino group in the compound of the formula XXI not by using hydrochloric acid, but enzymatically and thus enantioselectively. The enzymatic deacetylation is preferably carried out analogously to the enzymatic deacetylation of (RS)-N-acetylcyclohexylglycine described above, using the acylase "Amano" 30 000. In a particularly preferred procedure, the salt of the formula XXI isolated following the hydrogenation is initially dissolved in water and, after addition of a base, for example sodium hydroxide, stirred in the alkaline range, for example at a pH of from about 10 to about 11, to hydrolyze the methyl ester. Following addition of cobalt(II) chloride as co-catalyst, the acylase is added at a pH of from about 7.8 to about 7.9 and at a temperature of from about 38 to about 40° C., for example in an amount of from about 5 to about 6 g per kg of the compound of the formula XXI, and the mixture is stirred until the (S)-isomer is deacetylated. To convert the deacetylated (S)-isomer into the protected benzyloxycarbonylamino compound, then preferably, as illustrated above, a water-miscible solvent, such as THF, is added to the reaction mixture, the reaction with Z-OSu is carried out at a pH of from about 8.0 to about 8.5, the organic solvent is distilled off, the mixture is acidified to a pH of about 5 and the precipitated enantiomerically pure product of the formula XXII is then isolated.

The conversion of the Z-protected amino acid of the formula XXII into the Z-protected amino acid amide of the formula XXIII can be carried out using methods which are customary for such reactions and known to the person skilled in the art. According to a preferred method, the acid of the formula XXII is activated by conversion into the mixed anhydride using an alkyl chloroformate, particularly preferably isobutyl chloroformate. This reaction is preferably carried out in the presence of a tertiary amine, for example, N-ethyldiisopropylamine, in an ether such as THF as solvent, at temperatures of from about −10 to about 0° C., preferably from about −10 to about −5° C. Following this, ammonia is introduced, at a temperature of from about −10 to about 0° C., preferably from about −10 to about −5° C., into the solution of the mixed anhydride. After customary work-up and crystallization from a solvent, such as, for example, ethyl acetate, the compound of the formula XXIII is obtained in a yield of about 87%, with a chemical purity and enantiomeric purity of in each case virtually 100%.

The methylation of the pyridine nitrogen atom in the compound of the formula XXIII, with formation of the pyridinium salt of the formula XXIV, can be carried out smoothly with numerous methylating agents, for example methyl iodide, methyl bromide, methyl chloride or methyl toluene-4-sulfonate, in a number of solvents, for example alcohols, such as isopropanol, amides, such as DMF, N,N, N',N'-tetramethylurea, ketones, such as acetone, or ethers, such as THF, preferably at temperatures of from about 40 to about 60° C. In the reaction of the compound of the formula XXIII with methyl chloride in DMF at 45° C., for example, the compound of the formula XXIV where X=Cl is obtained in quantitative yield and a purity of about 98.4%. When the methylation is carried out on an industrial scale, it is preferred to use a less volatile methylating agent. Since an additional anion exchange, for example by ion exchange chromatography, is to be avoided if possible, a further aspect in the selection of the methylating agent is the effect of the anion X, contained in the compounds of the formulae IV, IX and I and originating from the methylating agent, on the properties of these compounds, for example on the solubility of the compound of the formula IV or a salt thereof, which is of importance in the coupling reaction of the compounds of the formulae III and IV, or on the solubilities, the precipitation properties and the physiological compatibility of the compound of the formula I. Overall, the iodides and toluene-4-sulfonates have, based on their properties, been found to be particularly favorable, preferred methylating agents thus being methyl iodide and methyl toluene-4-sulfonate (=methyl tosylate). The toluene-4-sulfonates, in particular, are distinguished, in the case of the compound of the formula IV or the toluene-4-sulfonic acid salt thereof, by the fact that they can be isolated easily, are highly soluble and have a high peptide coupling rate, and in the case of the compound of the formula I, in particular by surprisingly good precipitation properties, purity and yield. A particularly preferred methylating agent for the conversion of the compound of the formula XXIII into the compound of the formula XXIV thus is methyl toluene-4-sulfonate.

The methylation of the compound of the formula XXIII with methyl toluene-4-sulfonate is preferably carried out in a lower alcohol as solvent, for example in isopropanol, at temperatures of from about 40 to about 60° C., for example, at about 50° C. The methyl toluene-4-sulfonate is preferably employed in a small excess, for example in about 1 to about 1.2 times the molar amount, based on the compound of the formula XXIII. The methylation of the compound of the formula XXIII and the subsequent removal of the benzyloxycarbonyl protective group in the compound of the formula XXIV by hydrogenolysis can be carried out separately. Preferably, the methylation and hydrogenolysis are carried out in a one-pot reaction, without intermediate isolation of the compound of the formula XXIV. To this end, the compound of the formula XXIV is dissolved, for example by adding water, if it has precipitated from the reaction medium of the methylation, and then hydrogenated under customary conditions, for example in the presence of a customary noble metal catalyst, such as palladium on carbon, at temperatures from about 20 to about 40° C., preferably about 20 to about 30° C., and at a hydrogen pressure of from about 1 to about 20 bar, preferably from about 1 to about 5 bar, particularly preferably at about 1 bar, i.e. not under hydrogen overpressure. The monocation salt, comprising the 3-((S)-2-amino-2-carbamoylethyl)-1-methylpyridinium cation (having a free amino group $NH_2$ in the 2-position) and an anion X, for example tosylate, iodide or chloride, as counterion, i.e. the compound of the formula IV, can be isolated as such. Preferably, the resulting pyridinio-alaninamide is isolated in the form of a salt with the acid HX, i.e. in the form of the dication salt of the formula IX, and to this end, the reaction mixture of the hydrogenolysis is admixed with about one equivalent of the acid HX, i.e. about one equivalent of toluene-4-sulfonic acid in the case of the tosylate. The hydrogenation catalyst is filtered off, and the product can then be isolated by concentration and crystallization of the residue, for example from an alcohol such as isopropanol.

The present invention also provides the compounds of the formula IV in which X is an anion or anion equivalent, in particular a physiologically acceptable anion, for example, chloride, bromide, iodide or toluene-4-sulfonate, and their salts with the acid HX (=dication salts of the formula IX), per se, the above process for their preparation and processes in which one or more of the above steps are carried out, and their use as intermediates, in particular as intermediates of pharmaceutically active compounds, and the compounds of the formulae XX, XXI, XXII and XXIV per se.

The examples below serve to illustrate the present invention. However, the invention also embraces modifications of the embodiments described above and below, for example processes in which steps are combined into a one-pot process or, vice versa, a process is carried out in several separate steps, or where steps are carried out in a different order, or where similar reagents or solvents are used or where ratios or work-up methods are modified.

EXAMPLES

Example 1

4-(2-Methyl-5-oxooxazol-4-ylidenemethyl)benzonitrile

Acetone (80.0 l) was introduced into a mixture of 4-formylbenzonitrile (15.0 kg, 114.5 mol), N-acetylglycine (19.2 kg, 162.4 mol) and anhydrous sodium acetate (9.4 kg, 114.5 mol) followed by introduction, with stirring, of acetic anhydride (35.0 l, 370.5 mol). The reaction mixture was stirred under reflux for 1 h. The resulting thin yellow suspension was cooled to 50° C. and ice-water (200 l) was added as quickly as possible, with stirring and cooling. The mixture was stirred at 20° C. for another 1 h. To isolate the product, the yellow suspension was pressed onto a centrifuge and washed with deionized water (75 l), isopropanol (40 l) and methyl-tert-butylether (75 l). The product was dried under reduced pressure at 40° C. Yield 18.17 kg (85.7 mol, 75.2% of theory). M.p.: 192–193° C.; MS (DCI): m/z=213 [M+H$^+$]; $^1$H-NMR (DMSO-d$_6$): δ=2.42 (s, 3H), 7.30 (s, 1H), 7.96 (d, 2H), 8.33 (d, 2H).

Example 2

(R,S)-cyclohexylglycine

Under nitrogen, (R,S)-phenylglycine (10.0 kg, 66.2 mol) was added with stirring to water (78.5 l) and hydrochloric acid (30% strength, 21.5 l). Rhodium on carbon (209.6 g, G 101 S/W 5%, moistened with water, Degussa AG) was then added with stirring and under nitrogen. A hydrogen pressure of 18 bar was applied, and the mixture was heated to an internal temperature of 100° C. and stirred for 72 h. The mixture was then cooled to an internal temperature of 50° C. A TLC sample was taken (butanol/glacial acetic acid/water 2/1/1, R$_f$ [phenylglycine]=0.60, R$_f$ [cyclohexylglycine]= 0.68). After complete conversion, the catalyst was filtered off at 50° C. and the pH of the filtrate was, at 20° C., adjusted to pH 4 using aqueous sodium hydroxide solution (concentrated, about 15 l). The mixture was stirred for 30 min and the precipitated product was filtered off, washed twice with water (35 l each) and dried at 50° C. under reduced pressure. Yield: 9.7 kg (93% of theory). M.p.: >300° C.; MS (DCI): m/z (%)=158 ([M+H], 100); $^1$H-NMR (200 MHz, trifluoroacetic acid (TFA)): δ=1.1–1.6 (m, 5H), 1.7–2.1 (m, 5H), 2.1–2.3 (m, 1H), 4.3 (d, J=4 Hz, 1H), 11.6 (s, 1H); IR (KBr): ν=2927.7, 1583.9, 1508.8 cm$^{-1}$.

Example 3

(R,S)—N-Acetyl-cyclohexylglycine

At room temperature, (R,S)-cyclohexylglycine (9.41 kg, 61.7 mol) was added with stirring to an aqueous sodium hydroxide solution (concentrated, 30.2 l) in water (134 l). The mixture was cooled to an internal temperature of 5–10° C., and acetic anhydride (15.7 l, 17 kg, 166 mol) was metered in at this internal temperature over a period of 2 h (exothermic reaction). The pH was then checked and, if required, adjusted to at least pH=11 using aqueous sodium hydroxide solution. The mixture was stirred at an internal temperature of 5–10° C. for 1 h. The internal temperature was then increased to about 23° C., and stirring was continued for a further 2 h. Every hour, it was checked that the pH was still pH=11. After the reaction had ended (TLC, ethyl acetate/methanol/glacial acetic acid/water 70/30/5/5, R$_f$ [acetylcyclohexylglycine]=0.83, R$_f$ [cyclohexylglycine]= 0.55), the mixture was cooled to an internal temperature of 5–10° C. The pH was adjusted to pH=3 by slow addition of hydrochloric acid (30% strength, about 36 l), at an internal temperature of 5–10° C. Stirring was continued for a further 15 min, and the mixture was then filtered. The resulting solid was washed twice with water (45 l each) and dried at 60° C. under reduced pressure. Yield 11.52 kg (96.7% of theory). M.p. 195–197° C.; MS (DCI): m/z (%)=200.2 ([M$^+$+H], 100); $^1$H-NMR (200 MHz, DMSO-d$_6$): δ=0.9–1.3 (m, 5H), 1.5–1.8 (m, 6H), 1.86 (s, 3H), 4.1 (dd, J$_1$=8 Hz, J$_2$=6 Hz, 1H), 7.96 (d, J=8 Hz, 1H), 12.47 (s, 1H); IR (KBr): ν= 3339.7, 2929.3, 1699.9, 1615.7, 1563.2 cm$^{-1}$.

Example 4

(S)-Cyclohexylglycine by enzymatic deacetylation of (R,S)-N-acetyl-cyclohexylglycine At room temperature, (R,S)-N-acetylcyclohexylglycine (7.95 kg, 39.9 mol) was added with stirring to an aqueous sodium hydroxide solution (3.65 l, 33% strength) in water (143 l). With stirring, the pH was adjusted to pH 7.8 using hydrochloric acid (2N, about 0.8 l). Cobalt(II) chloride hexahydrate (13.8 g, 0.058 mol) was added with stirring. The mixture was then heated to an internal temperature of 38–40° C. At a constant internal temperature, acylase "Amano" 30 000 (40 g, in 400 ml of water) was added with slow stirring. The mixture was stirred slowly for 41 h, during which time the (S)-cyclohexylglycine slowly precipitated. Using hydrochloric acid (30% strength), the pH was carefully adjusted to pH 5.5–6.0. The mixture was cooled to an internal temperature of 2–5° C. and stirred for 1 h. The precipitated (S)-cyclohexylgycine was filtered off, washed with water (about 16 l) and dried under reduced pressure at 60° C. Yield: 2.79 kg (44.5%). M.p.>300° C.; [α]$_D$ 32.1° (c=1, 1N HCl); ee=99.78% (GC analysis on Chirasil L-Val following derivatization with propanol/HCl and perfluoropropionic anhydride); MS (DCl): m/z (%)=158 ([M$^+$+H], 100); $^1$H-NMR (200 MHz, TFA): δ=1.1–1.6 (m, 5H), 1.7–2.1 (m, 5H), 2.1–2.3 (m, 1H), 4.3 (d, J=4 Hz, 1H), 11.6 (s, 1H),.; IR (KBr): ν=2927.7, 1583.9, 1508.8 cm$^{-1}$.

To recover unreacted (R)-N-acetylcyclohexylglycine, the mother liquor was, at an internal temperature of 2–5° C., adjusted to pH=1 using hydrochloric acid (30% strength, about 4.3 l) and stirred at 2–5° C. for 1 h. The precipitated (R)-N-acetyl-cyclohexylglycine was filtered off, washed with water (about 16 l) and dried under reduced pressure at 60° C. Yield: 3.76 kg (47.3%). M.p. >210–212° C.; [α]$_D$– 23.5° (c=1, methanol); ee=98.39% (GC analysis of Chirasil L-Val following derivatization with propanol/HCl or methanol/HCl). $^1$H-NMR, MS and IR data agreed with the data of the racemic starting material 4.

Example 5

(R,S)-N-Acetylcyclohexylglycine by racemization of (R)-N-acetyl-cyclohexylglycine Under nitrogen, (R)-N-acetylcyclohexylglycine (10.9 kg, 54.7 mol) was admixed with stirring with glacial acetic acid (24.5 l) and acetic anhydride (1.7 l). The internal temperature was increased to 115° C., and the mixture was stirred at this temperature for 3.5 h. The internal temperature was then reduced to about 20° C., and water (73 l) was added. The pH of the reaction mixture was pH 2. The mixture was stirred at 0–3° C. for 1 h, the resulting solid was filtered off and washed twice with water (25 l each) and the substance was dried at 60° C. under reduced pressure. Yield: 7.95 kg (73% of theory) of (R,S)-N-acetylcyclohexylglycine. M.p. 195–196° C.; [α]$_D$ 0° (c=1, methanol). $^1$H-NMR, MS and IR data agreed with the data of the product obtained in Example 3. The mother liquor contained another about 2 kg of (R, S)-N-acetyl-cyclohexylglycine.

Example 6

(S)-Cyclohexylglycine by Racemization-Free Hydrogenation of (S)-phenylglycine

In a hydrogenation apparatus made of enamel or Hastelloy, (S)-phenylglycine (90 g, 0.53 mol; content of R-isomer <1%) was added at 50° C., under nitrogen and with stirring, to a solution of concentrated sulfuric acid (97% strength, 60 g) in deionized water (0.70 l). After all of the phenylglycine had been dissolved (if required, additional sulfuric acid (about 5 ml) was added), rhodium on carbon (6.3 g, 5%, moistened with water (50% water), from Engelhard type 5% RH Carb Polcere Escat 30 M, Engelhard Code 8000) was added. The hydrogenation apparatus was closed and inertized using nitrogen. The mixture was heated to an internal temperature of 80° C., and 20 bar of hydrogen were applied. The total hydrogenation time was 5–6 h, the hydrogen uptake was about 37 l. After the uptake of hydrogen had ended, the mixture was allowed to further hydrogenate at 20 bar for an extra 30–60 min. The mixture was then cooled to an internal temperature of 50° C., and the catalyst was filtered off at 50° C. using a pressure filter. The catalyst was washed with deionized water (0.30 l), and the filtrate was, at 20° C., adjusted to pH=4 by adding concentrated aqueous sodium hydroxide solution (33% strength, about 90 ml). Stirring was continued for 30 min, and the precipitated product was filtered off with suction and washed with deionized water (in total about 0.85 l) until the washings were free of sulfate ions. The moist product (about 150 g) was dried at 50° C. under reduced pressure. Yield: 80–84 g (86–90% of theory) of (S)-cyclohexylglycine. Optical purity: 99.3% ee.

Example 7

(S)-2-[2-Acetylamino-3-(4-cyanophenyl)acryloylamino]-2-cyclohexylacetic acid (S)-Cyclohexylglycine (3.14 kg, 20 mol) in acetone (70 l) was heated with stirring at 35° C. With stirring, 1 N aqueous sodium hydroxide solution (20 l) was then added over a period of 10 min. The mixture was heated to 40° C., and at an internal temperature of 40° C., solid 4-(2-methyl-5-oxooxazol-4-ylidenemethyl)benzonitrile (4.66 kg, 22 mol) was metered in in portions, with vigorous stirring, over 20 min. After the addition had been ended, the reaction mixture was stirred at an internal temperature of 40° C. for 1 h. The reaction solution was then filtered through a pressure nutsch covered with a Seitz filter K1000 and activated carbon (1 kg), and the filter residue was washed with 10 l of acetone. The filtrate was then cooled to 14° C. With stirring, 2N hydrochloric acid (about 10 l) was then added over a period of 10 min until a pH of 2.3 had been reached. Stirring was continued for 15 min, and the pH was readjusted using 2N HCl. Over a period of 20 min, the solution was then admixed with stirring with deionized water (160 l), whereupon the title compound precipitated. With stirring, the mixture was cooled to 0° C. and stirred at this temperature for 1 h. For isolation, the product was pumped onto a centrifuge, washed three times with water (10 l each), tumble-dried and dried at 40° C. under reduced pressure. Yield: 4.21 kg (11.4 mol, 57% of theory). M.p.: 196–198° C.; MS(ESI$^+$): m/z=370.2 [M+H$^+$]; $^1$H-NMR (200 MHz, DMSO-d$_6$): δ=0.98–1.35 (m 1.48–1.90 (m, 6H), 1.99 (s, 3H), 4.20 (dd, 1H), 6.98 (s, 1H), 7.72 (d, 2H), 7.88 (d, 2H), 8.02 (d, 1H), 9.58 (s, 1H), 12.65 (br s, 1H).

Example 8

(S)-2-[(S)-2-Acetylamino-3-(4-cyanophenyl)propionylamino]-2-cyclohexylacetic acid In an autoclave, (S)-2-[2-acetylamino-3-(4-cyanophenyl) acryloylamino]-2-cyclohexyl-acetic acid (7.94 kg, 21.5 mol) was initially charged in methanol (100.0 l) and the autoclave was carefully inertized using nitrogen. The catalyst solution was prepared as follows: methanol (3.0 l) was treated in an ultrasonic bath for 15 min during which time argon was introduced. With exclusion of oxygen, (+)-BPPM (10.92 g, 19.65 mmol) and [Rh(COD)Cl]$_2$ (4.88 g, 9.75 mmol) were then added successively, and the mixture was left in the ultrasonic bath for another 30 min. The yellow-orange catalyst solution was then pumped into the autoclave, with exclusion of oxygen.

About 3 bar of hydrogen were applied three times, and the autoclave was vented immediately again. The reaction mixture was heated to an internal temperature of 40° C., 10 bar of hydrogen were applied and the mixture was then hydrogenated with stirring at 40° C. for 20 h. The autoclave was then flushed with nitrogen. The hydrogenation solution was subsequently filtered through a Seitz filter. The filtrate was heated to 50° C., deionized water (110 l) was added over a period of 30 min, and stirring at 50° C. was continued for 1 h. The mixture was then cooled to 15° C. and stirred at 15° C. for 1 h. The precipitated product was isolated by filtration through a pressure nutsch filter, washed with deionized water (20 l) and dried under reduced pressure at 40° C. Yield: 7.73 kg (20.81 mol, 96.7% of theory). M.p.: 209–211° C.; MS (ESI$^+$): m/z=372.2 [M+H$^+$]; $^1$H-NMR (DMSO-d$_6$): δ=0.95–1.38 (m, 5H), 1.47–1.80 (m, 6H), 1.72 (s, 3H), 3.10 (2x dd, 2H), 4.15 (dd, 1H), 4.70 (m, 1H), 7.47 (d, 2H), 7.65 (d, 2H), 8.08 (d, 1H), 8.12 (d, 1H), 12.60 (br s, 1H).

Example 9

(S)-2-[(S)-2-Acetylamino-3-(4-amidinophenyl)propionylamino]-2-cyclohexylacetic acid betaine With stirring, methanol (20 l) was added to (S)-2-[(S)-2-acetylamino-3-(4-cyanophenyl)propionylamino]-2-cyclohexylacetic acid (3.77 kg, 10.1 mol) and hydroxylamine hydrochloride (1.06 kg, 15.2 mol). The mixture was stirred for 10 min, and sodium hydrogen carbonate (2.52 kg, 30 mol) was then added. Over a period of 1 h, the reaction mixture was heated slowly (evolution of carbon dioxide) to an internal temperature of 55° C. and then stirred at 55° C. for 6 h and stirred at room temperature overnight. The precipitated sodium chloride was filtered off with suction using a Seitz filter and washed with methanol (4 l). The methanol solution was concentrated to about 10 l using a rotary evaporator at a bath temperature of about 40° C., and added dropwise, with vigorous stirring, to isopropanol (60 l). This resulted in the precipitation of the sodium salt of the N-hydroxyamidine. To bring the precipitation to completion, the mixture was concentrated under reduced pressure, at about 40° C. and with vigorous stirring, to a volume of about 50 l. Stirring was then continued at 15° C. for 1 h, and the product was filtered off through a pressure nutsch. The precipitate was washed with isopropanol (10 l) and dried on the nutsch filter overnight, in a stream of nitrogen.

The resulting sodium salt of N-hydroxyamidine was then directly employed for the subsequent hydrogenation. To this end, glacial acetic acid (26 l) was initially charged in an autoclave, and the sodium salt of the N-hydroxyamidine (about 6.2 kg, moist crude product from the above reaction) was added in portions, with stirring. The solution was admixed with a suspension of palladium on carbon (10%, 50% water; 0.40 kg) in glacial acetic acid (1 l). The autoclave was flushed first with nitrogen and then with hydrogen, and the mixture was then hydrogenated at 50° C. and a hydrogen pressure of 18 bar for 72 h. The reaction mixture was allowed to cool to room temperature and filtered under nitrogen through a clarifying layer Seitz filter covered with activated carbon, and the filter residue was washed with glacial acetic acid (2 l). The filtrate was concentrated on a rotary evaporator at a bath temperature of 50° C. until no more glacial acetic acid distilled off and crystallization started. The mixture was then allowed to cool to about 25° C. and, whilst the mixture was still rotating, ethyl acetate (20 l) was soaked into the flask of the rotary evaporator, whereupon the amidine precipitated as acetic acid salt. After 0.5 h of extra stirring time, the precipitate was filtered off with suction by means of a paper filter and dried thoroughly with suction.

The crude amidinium acetate, obtained as described above, was introduced with vigorous stirring into deionized water (20 l) which had been heated to 40° C., and the mixture was heated at 80° C. until a clear solution had formed. With vigorous stirring, the mixture was then cooled to 15° C., within a period of 30 min, this resulting in the precipitation of the title compound (as betaine). Stirring was continued at 15° C. for 1 h, and the precipitated product was filtered off through a pressure nutsch. The filter cake was washed with ice-water (6 l), dried thoroughly in a stream of nitrogen, transferred into a vessel and stirred at room temperature and under nitrogen with 40 l of acetone for 1 h. The precipitated product was filtered off through a pressure nutsch, washed with acetone (about 10 l) and dried under reduced pressure at 40° C. Yield: 2.58 kg (6.64 mol, 65.7% of theory) of the title compound. MS (ESI$^+$): m/z=389.3 [M+H$^+$]; $^1$H-NMR (methanol-d$_4$): δ=0.98–1.38 (m, 5H), 1.58–1.78 (m, 6H), 1.96 (s, 3H), 3.10 (2x dd, 2H), 4.02 (d, 1H), 4.61 (dd, 1H), 7.42 (d, 2H), 7.68 (d, 2H).

Example 10

2-Methyl-4-[pyridin-3-yl-(Z)-methylene]-4H-oxazol-5-one

Under nitrogen, acetone (40.0 l), followed by pyridine-3-carbaldehyde (20.0 kg, 186.9 mol), was added to N-acetylglycine (32.7 kg, 280.0 mol) and sodium acetate (15.3 kg, 186.9 mol). With stirring, acetic anhydride (40.0 l, 429.0 mol) was added. Within 30 min, the reaction mixture was heated to reflux temperature and then stirred under reflux for 1.5 h. This gave a thin reddish suspension. The suspension was cooled to 50° C., and methyl tert-butyl ether (80.0 l) was then added. Ice-water (<2° C., 200.0 l) was added as quickly as possible (<5 min), with stirring and cooling, and the mixture was then stirred at 5–10° C. for 1 h. The beige suspension was introduced into a centrifuge which had been inertized with nitrogen. The precipitate was centrifuged, washed with deionized water (80.0 l) and dried under reduced pressure at 40° C. Yield: 24.8 kg (131.9 mol, 70.6% of theory). M.p.: 173° C.; MS (DCl): m/z (%)=189 ([M+H$^+$], 100); $^1$H-NMR (200 MHz, DMSO-d$_6$): δ=2.40 (s, 3H), 7.28 (s, 1H), 7.53 (dd, 1H), 8.61 (d, 2H), 9.18 (brs, 1H); IR (KBr): ν=1799.9, 1777.4, 898.0 cm$^{-1}$.

Example 11

3-(2-Acetylamino-2-methoxycarbonylvinyl)pyridinium tetrafluoroborate

Under nitrogen, a suspension of 2-methyl-4-[pyridin-3-yl-(Z)-methylene]-4H-oxazol-5-one (12.0 kg, 63.83 mol) in methanol (120.0 l) was heated at 60° C. Triethylamine (0.5 l) was pumped in, and the apparatus was rinsed with methanol (0.5 l) (the pH of a sample taken, measured using a glass electrode, was pH 8.15). Within a period of 30 min, the reaction solution was cooled to 30° C. Tetrafluoroboric acid solution (48% strength in water, 11.8 kg, 64.5 mol) was added over a period of 30 min. Within 1 h, the mixture was cooled to an internal temperature of 10° C. and (if required after seeding) the suspension was then stirred at 10° C. for a further 3 h. Methyl tert-butyl ether (40.0 l) was added, and the mixture was stirred at 10° C. for 1 h. The suspension was introduced into a centrifuge which had been inertized with nitrogen, centrifuged, and the the product washed with methyl tert-butyl ether (20.0 l) and dried at 40° C. under reduced pressure. Yield: 18.7 kg (60.71 mol, 95.1% of theory). M.p.: 179.4° C.; MS (ESI+): m/z (%)=221 ([M+H$^+$] of the free base, 100); $^1$H-NMR (200 MHz, DMSO-d$_6$): δ=2.01 (s, 3H), 3.77 (s, 3H), 7.21 (s, 1H), 7.89 (dd, 1H), 8.48 (d, 1H), 8.76 (d, 1H), 8.98 (s, 1H), 9.92 (s, 1H); IR (KBr): ν=1726.9, 1670.1, 1091.5 cm$^{-1}$.

Example 12

(S)-3-(2-Acetylamino-2-methoxycarbonylethyl)pyridinium tetrafluoroborate

In an autoclave, 3-(2-acetylamino-2-methoxycarbonylvinyl)pyridinium tetrafluoroborate (10.3 kg, 33.44 mol) was dissolved in methanol (120.0 l). Tetrafluoroboric acid solution (50% in water, 1.018 kg, 5.8 mol) was added, and the autoclave was closed and carefully inertized using nitrogen. The catalyst solution was prepared by treating methanol (3.0 l) in an ultrasonic bath for 15 min while introducing argon. With exclusion of air, the methanol degassed in this manner was admixed with (+)-phenyl-CAPP (12.5 g, 20.83 mmol) and [Rh(COD)Cl]$_2$ (5.0 g, 10.10 mmol), and the yellow-orange catalyst solution was sonicated under argon for 30 min. With exclusion of oxygen, the catalyst solution was introduced into the autoclave. Within a period of 1 h, the contents of the autoclave was heated to 40° C. In each case about 3 bar of hydrogen were applied three times, and the autoclave was vented immediately again. 1.5 bar of hydrogen were then applied, and the mixture was hydrogenated at 50° C., with vigorous stirring. After 7 h, the hydrogenation stopped. The HPLC analysis of a sample taken showed that, at this point in time, 99.1% of the title compound was present, and GC analysis (30 m fused silica capillary column Chirasil Val, isothermic 160° C., injector 220° C., detector (FID) 260° C., carrier gas 0.8 bar of hydrogen, $t_{ret}$ [(R) enantiomer] 12.64 min, $t_{ret}$ [(S) enantiomer] 13.64 min) showed that the enantiomeric purity was 86% ee of (S) isomer. The autoclave was flushed with nitrogen and, using nitrogen, the contents of the autoclave were pressed through a Seitz filter into a vessel, where the filtrate was stored at +5° C. under nitrogen.

Using the above procedure, four further asymmetric hydrogenations were carried out (batch size 8.0 kg (25.97 mmol)-10.3 kg (33.44 mol); hydrogen pressure 2–10 bar; temperature 40° C.; hydrogenation time 4–6 h; product content 98.0–99.8% (HPLC); enantiomeric purity of the crude product in the hydrogenation solution 62.0–84.5% ee of S isomer (GC)).

The filtrates of the five batches were combined and, at a jacket temperature of 40° C., concentrated under reduced pressure to the residual volume of 150 l. Isopropanol (200 l) was added, and the mixture was, at a jacket temperature of 40° C. and under reduced pressure, concentrated to a residual volume of 250 l. Two more times, isopropanol (in each case 100 l) was added, and the mixture was, at a jacket temperature of 40° C., concentrated to a residual volume of 250 l. This resulted in the crystallization of the title compound. The white suspension was stirred at 10° C. under nitrogen for 1 h. The product was centrifuged off using a centrifuge which had been inertized with nitrogen and was washed with isopropanol (100 l) and with methyl tert-butyl ether (150 l). This gave 45.0 kg (144.7 mol, 90.6% of theory) of the title compound with 71% ee of (S)-isomer (GC). M.p.: 126.2° C. (according to DSC); MS (ESI$^+$): m/z (%)=223 ([M+H$^+$] of the free base, 100); $^1$H-NMR (200 MHz, DMSO-d$_6$): δ=1.78 (s, 3H), 3.08 (dd, J=9.5 and 7 Hz, 1H), 3.29 (dd, J=9.5 and 4 Hz, 1H), 4.68 (m, 1H), 8.00 (dd, J=5.0 and 4.5 Hz, 1H), 8.42 (t or 2 d, J about 6 Hz, 2H), 8.80 (d, J about 5 Hz, 1H), 8.82 (s, 1H); IR (KBr): ν=1740.9, 1654.3 cm$^{-1}$.

Example 13

(S)-2-Benzyloxycarbonylamino-3-(pyridin-3-yl)propionic acid

A solution of (S)-3-(2-acetylamino-2-methoxycarbonylethyl)pyridinium tetrafluoroborate (71% ee; 6.70 kg, 21.6 mol) in water (88 l) was filtered through a pressure nutsch covered with activated carbon (0.5 kg). Using concentrated aqueous sodium hydroxide solution (33% strength, about 3.0 l), the pH of the filtrate was adjusted to pH 10–11, and the solution was then stirred at 20–25° C. for 2 h, during which the pH was kept constant using concentrated aqueous sodium hydroxide solution. TLC (mobile phase ethyl acetate/methanol/water/acetic acid 70/30/5/5) showed that the methyl ester had been hydrolyzed completely to give the carboxylic acid. Using concentrated hydrochloric acid (about 150 ml), the pH was adjusted to pH 8.0. Cobalt(II) chloride hexahydrate (11.7 g, 0.049 mol) was added, and the reaction mixture was heated to an internal temperature of 40° C. and stirred at a constant temperature of 39° C. for 1 h. With very slow stirring, acylase "Amano" 30 000 (38.0 g) in deionized water (400 ml) was added at 39° C., and the mixture was then stirred at a constant pH of 7.9 and a constant temperature of 39° C. for 40 h. TLC (mobile phase as above) confirmed that about 85% of the carboxylic acid (corresponding to the content of (S) isomer in the 3-(2-acetylamino-2-methoxycarbonylethyl)pyridinium tetrafluoroborate used) had been deacetylated. The vessel was inertized with nitrogen, and tetrahydrofuran (22.0 l) was then added and the reaction mixture was, over a period of 1 h, cooled to an internal temperature of 10° C. Within 45 min, a solution of N-(benzyloxycarbonyloxy)succinimide (4.63 kg, 18.6 mol) in tetrahydrofuran (23.0 l) was added, during which time the pH was kept at 8.0–8.5 by continuous addition of concentrated aqueous sodium hydroxide solution (33% strength). The mixture was then stirred at 20° C. for 1.5 h. TLC (mobile phase as above) showed complete acylation of the free amino acid. Ethyl acetate (60 l) was added to the reaction mixture, which was then stirred vigorously for 15 min. After thorough phase separation, the ethyl acetate phase was separated off and discarded. The aqueous phase was adjusted to pH 5.0 using concentrated hydrochloric acid (about 3.7 l), seed crystals of the enantiomerically pure title compound were added and the suspension was then stirred at 5° C. overnight. Under nitrogen, the crystals were filtered off through a pressure nutsch, washed with deionized water (20 l) and dried at 48° C. under reduced pressure. Yield: 2.86 kg (9.52 mol, 51.9% of theory) of the title compound with 100% ee (CSP Chiralpak AD 250×4.6 mm Daicel; mobile phase: isopropanol/ethanol/n-hexane 12/4/84+0.1% diethylamine; $t_{ret}$ 14.16 min), [α]$_D$– 9.95° (c=1.0, methanol). M.p.: 173–174° C. (by DSC); MS (ESI$^+$): m/z (%)=301 ([M+H$^+$], 100); $^1$H-NMR (200 MH DMSO-d$_6$): δ 2.85 (dd, J=9.5 and 7.5 Hz, 1H), 3.10 (dd, J=9.5 and 3.5 Hz, 1H), 4.23 (m, 1H), 4.98 (s, 2H), 7.15–7.40 (m, 6H), 7.62–7.78 (m, 2H), 8.38–8.50 (m, 2H), 12.80 (brs, 1H); IR (KBr): ν=3369.7, 1707.4, 1504.7, 1046.9, 699.2 cm$^{-1}$.

Example 14

Benzyl (S)-[1-carbamoyl-2-(pyridin-3-yl)-ethyl] carbamate

A suspension of (S)-2-benzyloxycarbonylamino-3-(pyridin-3-yl)propionic acid (2.60 kg, 8.65 mol) in tetrahydrofuran (60 l) was cooled to –9° C. At this temperature, N-ethyldiisopropylamine (1.33 kg, 10.29 mol) was added over a period of 5 min. At –9° C., isobutyl chloroformate (1.36 kg, 9.96 mol) was then added within 20 min, the internal temperature in the end increasing to –6° C. After 10 min of vigorous stirring, ammonia gas (2.1 kg, about 123 mol) was introduced at a constant temperature of (–5)–(–6)° C. into the resulting thin suspension in the course of 3 h. The reaction was initially strongly exothermic (requires initially slow introduction), later on less exothermic. Over a period of 30 min, the reaction mixture was warmed to 16° C., which gave a thick but still stirrable crystal slurry. At a jacket temperature of 30° C., the solvent was removed under reduced pressure. The white, greasy residue was suspended in ethyl acetate (125 l). A solution of sodium hydrogen carbonate (3.0 kg) in water (50 l) was added and the mixture was stirred vigorously for 30 min, after which all of the solid had dissolved. The organic phase was separated off and dried over sodium sulfate (1.0 kg), the drying agent was filtered off and the filtrate was concentrated under reduced pressure at a bath temperature of 30° C. to a volume of about 6 l. The resulting precipitate was filtered off with suction, washed with ethyl acetate (1.5 l) and dried at 30° C. under reduced pressure. Yield: 2.26 kg (7.55 mol, 87.3% of theory). The chemical purity was 99.9% (HPLC: 125×4.0 mm RP18 Purospher, 40° C., detection 210 nm); the enantiomeric purity was 100% ee (HPLC: 250×4.6 mm CSP Chiralpak AD Daicel, 40° C.; detection 248 nm; mobile phase: n-hexane/isopropanol/ethanol 84/12/4+0.1% diethylamine; $t_{ret}$ [(S)-isomer] 14.93 min). M.p.: 152.8° C. (by DSC); MS (ESI$^+$): m/z (%): 300 ([M+H$^+$], 100); $^1$H-NMR (200 MHz, DMSO-d$_6$): δ=2.77 (dd, J=9.5 and 7.0 Hz, 1H), 3.02 (dd, J=9.5 and 3.5 Hz, 1H), 4.19 (m, 1H), 4.96 (s, 3H), 7.00–7.40 (m, 7H), 7.40–7.60 (m, 2H), 7.60–7.76 (m, 1H), 8.36–8.53 (m, 2H); IR (KBr): ν=3306.8, 1674.9, 1537.7, 1424.0, 1271.6, 1251.3 cm$^{-1}$.

Example 15

3-((S)-2-Ammonio-2-carbamoylethyl)-1-methylpyridinium ditosylate

In an autoclave, isopropanol (1.7 l) was added to benzyl (S)-[1-carbamoyl-2-(pyridin-3-yl)ethyl]carbamate (1.00 kg, 3.33 mol) and methyl toluene-4-sulfonate (0.67 kg, 3.6 mol), the stirrer was started and the reaction mixture was stirred in the closed autoclave, at 50° C. and under nitrogen, for 5 h. The reaction mixture was allowed to stand at room temperature overnight, which resulted in the sedimentation of the methylated N-benzyloxycarbonyl compound as a viscous slime. The reaction solution was diluted with deionized water (0.33 l), and palladium/carbon (10%, 50% water; 50 g) was then added. The hydrogenation was carried out under atmospheric pressure by passing through hydrogen (about 10 l/min), with continuous metered addition of a solution of toluene-4-sulfonic acid monohydrate (0.63 kg, 3.33 mol) in deionized water (1.0 l) at 20–25° C., over a period of about 3 h. After the hydrogenation had ended, the autoclave was flushed with nitrogen and the hydrogenation solution was filtered through a Seitz filter and washed with deionized water (0.5 l). The filtrate was transferred into a rotary evaporator and concentrated under steam-jet vacuum at a bath temperature of 40° C. to about 2.5 l. With vigorous stirring, isopropanol (10 l) was then soaked in and the mixture was, with stirring under reduced pressure at a bath temperature of 40° C., concentrated to about 5 l whereupon the title compound started to crystallize. With stirring, the crystal suspension was cooled at 15° C. for 0.5 h, and the product was filtered off with suction through a paper filter, washed with 1 l of isopropanol, dried thoroughly with suction and dried. Yield: 1.57 kg (3.0 mol, 90% of theory). M.p.: 219–220° C.; MS (ESI$^+$): m/z (%)=180.1 ([M+H$^+$], 100); $^1$H-NMR (DMSO-d$_6$): δ 2.30 (s, 3H), 3.10–3.40 (m, 2H), 4.08 (dd, 1H), 4.35 (s, 3H), 7.12 (d, 4H), 7.48 (d, 4H), 7.70 (s, 1H), 7.90 (s, 1H), 8.05–8.22 (m, 4H), 8.42 (m, 1H), 8.95 (m, 1H).

Example 16

3-{(S)-2-[(S)-2-((S)-2-Acetylamino-3-(4-amidiniophenyl)propionylamino)-2-cyclohexylacetylamino]-2-carbamoylethyl}-1-methylpyridinium ditosylate Under nitrogen, 3-hydroxy-4-oxo-3,4-dihydro-1,2,3-benzotriazine (1.306 kg, 30.0% on Dicalite®, 2.40 mol) was added to a suspension of 3-((S)-2-ammonio-2-carbamoylethyl)-1-methylpyridinium ditosylate (5.43 kg, 10.36 mol) and (S)-2-[(S)-2-acetylamino-3-(4-amidinophenyl)propionylamino]-2-cyclohexylacetic acid betaine (4.00 kg, 93.15% pure, water content 6.85%, 9.591 mol) in N,N-dimethylformamide (45.0 l), and the suspension was cooled to 10° C. At this temperature, at a uniform rate, a solution of dicyclohexylcarbodiimide (2.56 kg, 99% pure, 12.28 mol) in N,N-dimethylformamide (3.4 l) was added over a period of 7 h by means of a pump, and pump and tubes were then rinsed with N,N-dimethylformamide (0.5 l). The mixture was stirred at 10° C. for 1 h and then, with warming to room temperature (23.5° C.), for a further 14 h. The suspension was filtered through a Seitz layer and washed with a mixture of N,N-dimethylformamide (2.2 l) and toluene (0.2 l). Over a period of 30 min, the filtrate was pumped into a vessel which had been initially charged with acetone (1200 l), which was stirred vigorously under nitrogen, at 18° C. The mixture was stirred at room temperature for 10 min and the suspension was then pressed with nitrogen through a pressure nutsch which had been covered with a filter cloth made of polypropylene and a Seitz filter. The residue was washed with acetone (3×100 l), the solid on the pressure nutsch was dried overnight using nitrogen, and the precipitation of the product from acetone was then repeated. To this end, the solid was dissolved with stirring in N,N-dimethylformamide (25 l) and the solution was admixed with toluene (2.5 l) and, over a period of 15 min, pumped into a vessel which had been initially charged with acetone (1200 l), which was stirred vigorously under nitrogen, at 18° C. The suspension was stirred at room temperature for 10 min and then pressed with nitrogen through a pressure nutsch. The residue was washed with acetone (3×100 l). The solid was dried thoroughly in a stream of nitrogen and then dried initially at 20° C. under reduced pressure and then at 43° C. under high vacuum. Yield: 7.83 kg (8.76 mol, 91.3% of theory). The enantiomeric purity was >99% ee (HPLC: CSP Chiral AGP 100×4.0 mm 5 μm; 40° C., 0.7 ml/min aqueous sodium acetate solution (100 mM); $t_{ret}$ 6.20 min, $t_{ret}$ [enantiomer] 4.26 min, $t_{ret}$ [diastereomer] 4.97 min); [a]$_D^{25}$ –6.50 (c=1.0, water). The chemical purity was 97%, the content of diastereomer was 2.4% (HPLC: Superspher 60 RPselect B 250×4.0 mm; 25° C.; detection 210 nm; 1.0 ml/min; mobile phase A: 950 ml of water+50 ml of acetonitrile+7 ml of orthophosphoric acid, adjusted to pH 3 with about 8 ml of triethylamine, mobile phase B: 600 ml of water+400 ml of acetonitrile+7 ml of orthophosphoric acid, adjusted to pH 3 with about 8 ml of triethylamine; elution program: 15 min of 100% mobile phase A, then over a period of 10 min linear to 50% mobile phase A+50% mobile phase B, then for a further 15 min isocratically this 50:50 mixture of the mobile phases: $t_{ret}$ [title cation] 13.44 min, $t_{ret}$ [tosylate anion] 26.88 min). MS (FAB, NBA): m/z (%)=722 ([M$^+$] of the monotosylate, 15%), 550 ([M$^+$] of the tosylate-free monocation (N-methylpyridiniumamidine), 100%); $^1$H-NMR (500 MHz, DMSO-d$_6$): δ=0.80–1.25 (m, 6H), 1.40–1.70 (m, 5H), 1.72 (s, 3H), 2.29 (s, 6H), 2.71 (d, 1H), 2.98–3.07 (m, 3H), 3.18 (dd, 1H), 4.05 (t, 1H), 4.36 (s, 3H), 4.55–4.65 (m, 2H), 7.11 (d, 4H), 7.27 (s, 1H), 7.42 (s, 1H), 7.47 (d, 4H), 7.51 (d, 2H), 7.73 (d, 2H), 7.92 (d, 1H), 8.06 (dd, 1H), 8.21 (d, 1H), 8.40 (d, 1H), 8.88 (m, 4H), 9.25 (s, 2H); $^{13}$C-NMR (75.43 DMSO-d$_6$, {$^1$H}-broad-band decoupled): δ=20.67 (2C), 22.31 (1C), 25.51 (2C), 25.65 (1C), 28.32 (1C), 28.89 (1C), 34.21 (1C), 36.95 (1C), 47.79 (1C), 52.19 (1C), 57.67 (1C), 125.36 (4C), 125.80 (1C), 126.82 (1C), 127.70 (1C), 128.03 (4c), 129.59 (1C), 137.74 (2C), 138.13 (1C), 143.36 (1C), 144.68 (1C), 145.25 (2C), 145.37 (1C), 145.63 (1C), 165.16 (1C), 169.26 (1C), 170.58 (1C), 171.35 (2C); IR (KBr):ν=3286, 1663, 1184, 1124, 1035, 1011, 683, 569 cm$^{-1}$.

The invention claimed is:

1. A process for the preparation of a compound of the formula I, which comprises:
    (a) converting a compound of the formula II into a compound of the formula III or its salt with an acid HX, said converting comprises catalytic hydrogenation of the olefinic group and conversion of the cyano group into an amidino group to yield the compound of formula III or its salt with the acid HX, and
    (b) reacting the compound of the formula III or its salt with the acid HX with a compound of the formula IV or its salt with the acid HX to yield a compound of the formula I,
    wherein the anions X$^-$ of the formulae I and IV and of the acid HX are physiologically acceptable anions, and are identical or different

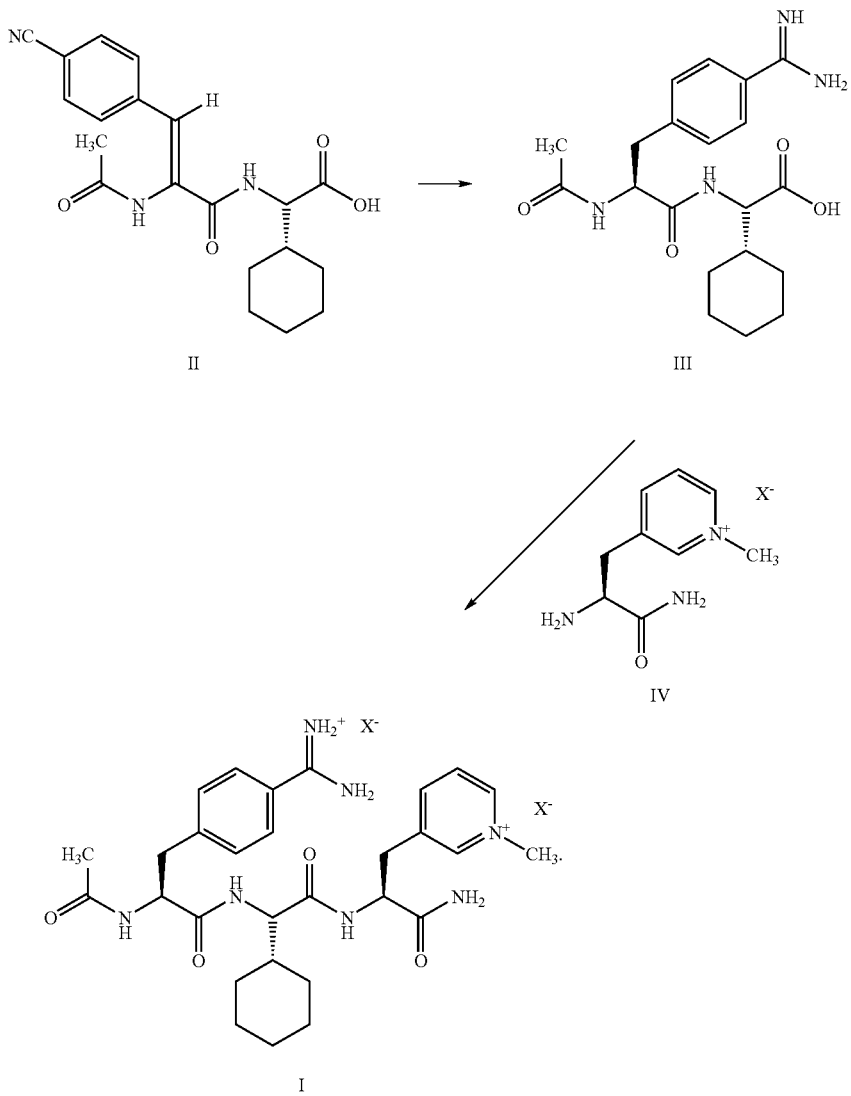

2. The process as claimed in claim 1, wherein the anions X$^-$ of the formulae I and IV and of the acid HX are identical.

3. The process as claimed in claim 1, which comprises employing in the catalytic hydrogenation a catalyst, the catalyst comprising a chiral rhodium(I) complex.

4. The process as claimed in claim 3, wherein the chiral rhodium(I) complex comprises a rhodium(I)-(+)-(2R,4R)-1-tert-butyloxycarbonyl-4-diphenylphosphino-2-(diphenylphosphinomethyl)pyrrolidine complex.

5. The process as claimed in claim 1, wherein the conversion of the cyano group into the amidino group comprises reacting the cyano group with hydroxylamine or an hydroxylammonium salt to yield a resulting N-hydroxyamidine, and hydrogenolysing the resulting N-hydroxyamidine.

6. The process as claimed in claim 1, wherein said reacting is carried out in the presence of a carbodiimide.

7. The process as claimed in claim 1, wherein said reacting is carried out in the presence of dicyclohexylcarbodiimide and 3-hydroxy-4-oxo-3,4-dihydro-1,2,3-benzotriazine.

8. The process as claimed in claim 1, wherein in said reacting, the compound of the formula IV is employed in the form of its salt with the acid HX, and the compound of the formula III is employed in free form.

9. The process as claimed in claim 1, wherein the anions X⁻ of the formulae I and IV and of the acid HX are toluene-4-sulfonate.

10. The compound of the formula Ia in which the anion TosO⁻ is toluene-4-sulfonate

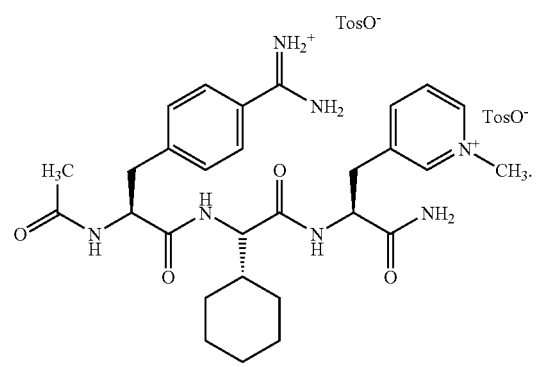

Ia

11. A process for preparing a compound of the formula Ia in which the anion TosO⁻ is toluene-4-sulfonate, which process comprises:

reacting a compound of the formula III or the toluene-4-sulfonic acid salt thereof with a compound of the formula IVa or the toluene-4-sulfonic acid salt thereof to yield the compound of the formula Ia

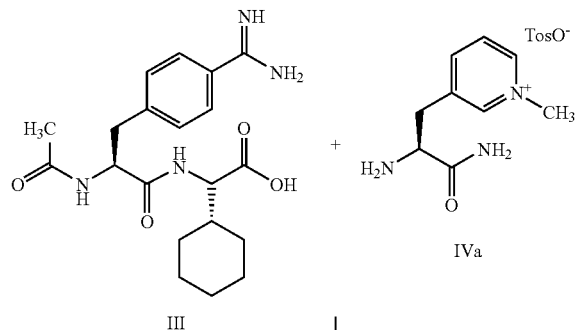

III          IVa

↓

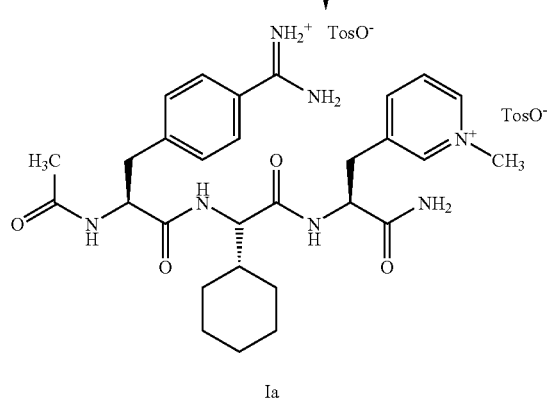

Ia

12. The process as claimed in claim 11, wherein the compound of the formula IVa is employed in the form of its salt with toluene-4-sulfonic acid and the compound of the formula III is employed in free form, and the reacting is carried out in the presence of dicyclohexylcarbodiimide and 3-hydroxy-4-oxo-3,4-dihydro-1,2,3-benzotriazine.

13. A compound of the formula II or a salt thereof

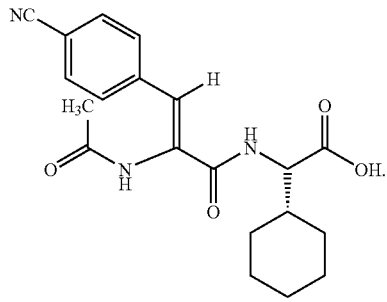

II

14. A compound of the formula III or a salt thereof

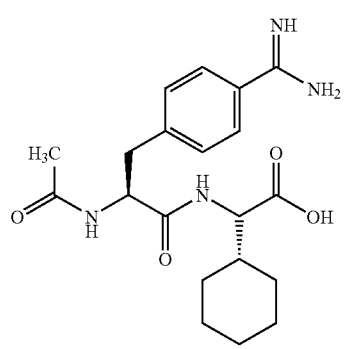

III

15. A compound of the formula IV where the anion X⁻ is a physiologically acceptable anion, or a salt thereof.

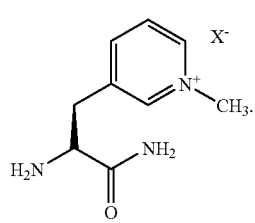

IV

16. A process for the preparation of a compound of the formula I':

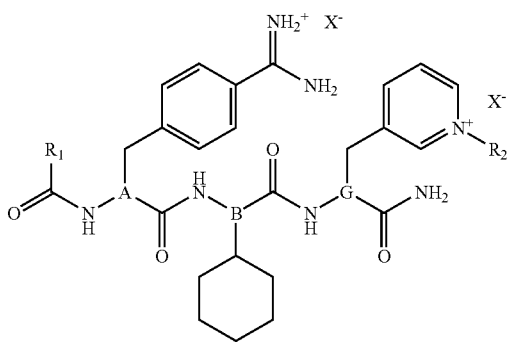

I' wherein
- $R_1$ is $C_1$–$C_4$ alkyl;
- $R_2$ is $C_1$–$C_4$ alkyl;
- A is CH in the R or S configuration;
- B is CH in the R or S configuration; and
- G is CH in the R or S configuration, the process comprising:

(a) converting a compound of the formula II' into a compound of the formula III' or its salt with an acid HX, the compound of the formula II' having the structure:

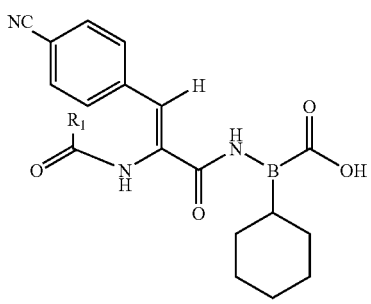
II' wherein
$R_1$ and B have the same meanings as in the formula I',
said converting comprises catalytic hydrogenation of the olefinic group and conversion of the cyano group into an amidino group to yield the compound of the formula III' or its salt with an acid HX;
the compound of the formula III' having the structure:

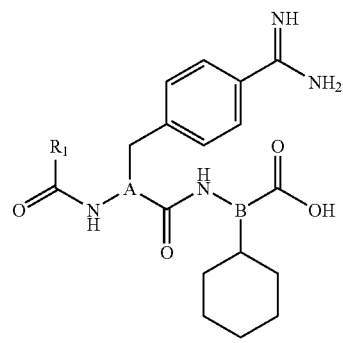
III' wherein
$R_1$, A, and B have the same meanings as in the formula I'; and (b) reacting the compound of the formula III' or its salt with the acid HX with a compound of the formula IV' or its salt with the acid HX:

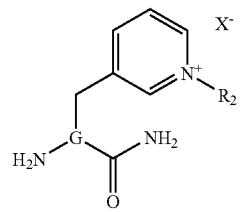
IV' wherein
$R_2$ and G have the same meanings as in the formula I',
to yield a compound of the formula I',
wherein the anions $X^-$ of the formula I' and IV' and of the acid HX are physiologically acceptable anions, and are identical or different.

* * * * *